(12) United States Patent
Parry et al.

(10) Patent No.: US 9,241,801 B1
(45) Date of Patent: Jan. 26, 2016

(54) JOINT ARTHROPLASTY

(71) Applicant: Todd R. Parry, Saint George, UT (US)

(72) Inventors: Todd R. Parry, Saint George, UT (US); David M. Skinlo, North Logan, UT (US); Ephraim Akyuz, Logan, UT (US)

(73) Assignee: Todd R. Parry, Saint George, UT (US)

( * ) Notice: Subject to any disclaimer, the term of this patent is extended or adjusted under 35 U.S.C. 154(b) by 0 days.

(21) Appl. No.: 14/202,286

(22) Filed: Mar. 10, 2014

Related U.S. Application Data

(63) Continuation of application No. 14/093,007, filed on Nov. 28, 2013, now abandoned, which is a continuation-in-part of application No. 13/032,386, filed on Feb. 22, 2011, now abandoned.

(51) Int. Cl.
A61F 2/38 (2006.01)
A61F 2/30 (2006.01)

(52) U.S. Cl.
CPC .............. *A61F 2/389* (2013.01); *A61F 2/30749* (2013.01); *A61F 2/3859* (2013.01); *A61F 2002/3069* (2013.01); *A61F 2002/3093* (2013.01); *A61F 2002/30561* (2013.01); *A61F 2002/30599* (2013.01); *A61F 2002/30616* (2013.01); *A61F 2002/30617* (2013.01); *A61F 2002/30736* (2013.01); *A61F 2002/30772* (2013.01); *A61F 2002/30777* (2013.01); *A61F 2002/30779* (2013.01); *A61F 2002/30784* (2013.01); *A61F 2002/30841* (2013.01); *A61F 2002/30922* (2013.01)

(58) Field of Classification Search
CPC ............ A61F 2002/30324; A61F 2002/30734; A61F 2/38; A61F 2/389; A61F 2002/30736

USPC .............. 623/20.14–20.17, 20.21–20.31, 623/20.32–20.36, 23.48, 23.62
See application file for complete search history.

(56) References Cited

U.S. PATENT DOCUMENTS

| | | | |
|---|---|---|---|
| 4,298,993 A | 11/1981 | Kovaleva et al. | |
| 4,731,086 A * | 3/1988 | Whiteside et al. | 623/20.16 |
| 5,047,058 A | 9/1991 | Roberts et al. | |
| 5,092,883 A | 3/1992 | Eppley et al. | |
| 5,152,797 A * | 10/1992 | Luckman et al. | 623/20.16 |
| 5,207,711 A * | 5/1993 | Caspari et al. | 623/20.3 |
| 5,344,461 A * | 9/1994 | Phlipot | 623/20.16 |
| 5,387,241 A | 2/1995 | Hayes | |
| 5,458,637 A * | 10/1995 | Hayes | 623/16.11 |
| 5,766,251 A | 6/1998 | Koshino | |
| 7,547,327 B2 * | 6/2009 | Collazo | 623/20.16 |
| 2004/0030397 A1* | 2/2004 | Collazo | 623/20.32 |
| 2004/0162619 A1* | 8/2004 | Blaylock et al. | 623/20.16 |

(Continued)

*Primary Examiner* — Marcia Watkins
(74) *Attorney, Agent, or Firm* — Maywood IP Law; David Meibos

(57) ABSTRACT

A system and method for joint arthroplasty may utilize one or more scaffolds to help support an arthroplasty prosthesis for the joint. A natural or prosthetic articulating surface may first be removed from one of the bones of the joint. This may expose a resection surface. A target portion of the resection surface may be identified based on, for example, fit and function testing of the joint with a trial arthroplasty prosthesis in place on the resection surface. One or more scaffolds may be placed on the target portion, and bone cement may be positioned adjacent to the scaffold(s) to define a raised surface that provides better fit and/or function than that which would be obtained with placement on the recessed surface. The arthroplasty prosthesis may be secured to the raised surface through the use of the bone cement.

15 Claims, 28 Drawing Sheets

(56) References Cited

U.S. PATENT DOCUMENTS

| | | |
|---|---|---|
| 2005/0203634 A1* | 9/2005 | Bassik et al. ............... 623/22.42 |
| 2007/0088443 A1* | 4/2007 | Hanssen et al. ............ 623/23.46 |
| 2007/0129809 A1 | 6/2007 | Meridew et al. |
| 2007/0179607 A1 | 8/2007 | Hodorek et al. |
| 2007/0179627 A1* | 8/2007 | Gustilo et al. ............. 623/20.15 |
| 2007/0213830 A1 | 9/2007 | Ammann et al. |
| 2009/0157190 A1* | 6/2009 | Collazo et al. ............. 623/20.32 |
| 2010/0016981 A1* | 1/2010 | Roger ........................ 623/20.32 |
| 2012/0185053 A1 | 7/2012 | Berger |

* cited by examiner

JOINT ARTHROPLASTY

CROSS-REFERENCE TO RELATED APPLICATIONS

The present application is a continuation of U.S. patent application Ser. No. 14/093,007, entitled JOINT ARTHROPLASTY SYSTEMS AND METHODS, which was filed on Nov. 28, 2013, which is continuation-in-part of U.S. patent application Ser. No. 13/032,386, entitled ARTHROPLASTY SHIM, which was filed on Feb. 22, 2011. All of the foregoing are incorporated by reference as though set forth herein in their entirety.

TECHNICAL FIELD

The present invention relates to orthopedic medical devices and methods. More specifically, the present invention relates to systems and methods for facilitating joint arthroplasty.

BACKGROUND

The proper functioning of a joint, such as the knee, hip, shoulder, ankle or elbow can be impeded by a variety of factors, including, disease, such as osteoarthritis, mechanical injury, bone deformation and a variety of other factors. Arthroplasty, or the surgical restoration of a joint, j is a known procedure that is often used to relieve pain and improve joint function by replacing the diseased or damaged articulating surfaces of a joint with prosthetic components. Achieving joint balance is a primary goal for arthroplasty surgeons. A balanced joint is a joint that has the proper articulation in all orientations of the joint. The patient may be most comfortable when the artificial joint replicates the kinematics of the original, natural joint.

One of the most common arthroplasty procedures is knee replacement surgery. Some common forms of knee replacement surgery include total knee replacement ("TKR") surgery; partial knee replacement surgery, which is also known as unicompartmental arthroplasty ("UKA"); and revision knee surgery; each of which is briefly described below.

Generally, in a TKR, the femur's lateral and medial condyles, or the articulating surfaces at the femur's distal end, are removed and replaced with a femoral prosthetic component. Additionally, in a TKR, the tibial plateau at the tibia's proximal end is also removed and replaced with a tibial prosthetic component.

In contrast, during a UKA, the knee is generally divided into three compartments—namely a medial compartment that is located at the inside of the knee, a lateral compartment that is located at the outside part of the knee, and a patellofemoral compartment that is located between the kneecap and the femur. In a UKA where the damage is confined primarily to one compartment (namely the medial or lateral compartment), the articulating surfaces from that particular compartment of the femur and/or tibia are usually removed and replaced with prosthetic components.

With respect to revision knee surgery, such surgeries generally involve removing one or more prosthetic components that were previously placed within the knee ("primary components") but have become worn, did not fit properly, or have otherwise prevented the knee from functioning properly. The primary components are then typically replaced with one or more replacement components ("revision prosthetic components").

Joint replacement surgery involves exposing the joint, preparing the surfaces, correcting any misalignment, and creating the appropriate tension on the constraining ligaments to allow the components to move through a smooth balanced arch of motion. If there is lack of tension holding one side of the joint together compared to the amount of tension on the other side, this creates an imbalance and an opening of the loose side of the joint when moves through its range of motion. A patient can often feel this extra motion, laxity, and/or imbalance as a sense of instability in the joint and it can contribute to patient dissatisfaction as well as a joint that wears out faster as it is not restrained to the smooth motion it was engineered to follow.

A surgeon needs to balance the space into which he is placing a component so that the medial space will match the lateral space, in both the flexed and extended positions of the joint. This will result in equal contact pressures throughout the joint as it is moved back and forth through flexion and extension. The surgeon can alter the shape of the exposed bone surface, tighten or loosen the ligamentous restraint on each side of the joint, or alter the size of the components he is using to replace the joint.

Techniques currently used to balance the joint have significant drawbacks. For example, in some circumstances, surgeons will cut away or remove more bone from the tight side of the joint to open this space to match the space on other side. Another technique is to release or stretch the tensioning ligament on the tight side of the joint to allow it to open up and match the looser side. With these cut or release techniques there is always the risk of removing too much bone or over releasing the ligament to the point of failure. These problems can be difficult to correct, and can result in increased surgical and recovery time. Furthermore, a wider range of joint components may be needed to accommodate these iatrogenic conditions.

SUMMARY OF THE INVENTION

The various systems and methods of the present invention have been developed in response to the present state of the art, and in particular, in response to the problems and needs in the art that have not yet been fully solved by currently available joint arthroplasty systems and methods. The systems and methods of the present invention may enable joint arthroplasty that provides superior fit and function of the replacement joint, without the need for additional risk, trauma, and recovery time.

To achieve the foregoing, and in accordance with the invention as embodied and broadly described herein, a system and method for joint arthroplasty may utilize one or more scaffolds to help support an arthroplasty prosthesis for the joint. A natural or prosthetic articulating surface may first be removed from one of the bones of the joint. This may expose a resection surface. A target portion of the resection surface may be identified based on, for example, fit and function testing of the joint with a trial arthroplasty prosthesis in place on the resection surface. By elevating a side of the arthroplasty prosthesis above its current trial position, a surgeon may tighten the loose side and achieve a balanced joint while avoiding the need to either cut bone or loosen ligaments on the tight side. The exact location on the bone surface where the surgeon determines an elevating element or scaffold could be used will be referred to as the target portion of the bone.

One or more scaffolds may be placed on the target portion, and bone cement may be positioned adjacent to the scaffold(s). The scaffold(s) may help to hold the cement in place such that, when the cement hardens, it may define a raised surface that provides better fit and/or function than that which would be obtained with placement on the unmodified resection surface. The arthroplasty prosthesis may be secured to the raised surface through the use of the bone cement.

Thus, the joint may be balanced without the need to further remove healthy bone tissue, loosen healthy ligaments, or the like. By using substance addition methods to build up the host bone instead of exclusively subtracting tissue, the likelihood of repeated adjustment of the fit and function prior to attachment of the final arthroplasty prosthesis may be reduced, thereby cutting down on operative time and the risk of errors.

These and other features and advantages of the present invention will become more fully apparent from the following description and appended claims, or may be learned by the practice of the invention as set forth hereinafter.

BRIEF DESCRIPTION OF THE DRAWINGS

Exemplary embodiments of the invention will become more fully apparent from the following description and appended claims, taken in conjunction with the accompanying drawings. Understanding that these drawings depict only exemplary embodiments and are, therefore, not to be considered limiting of the invention's scope, the exemplary embodiments of the invention will be described with additional specificity and detail through use of the accompanying drawings in which:

DETAILED DESCRIPTION

Exemplary embodiments of the invention will be best understood by reference to the drawings, wherein like parts are designated by like numerals throughout. It will be readily understood that the components of the invention, as generally described and illustrated in the Figures herein, could be arranged and designed in a wide variety of different configurations. Thus, the following more detailed description of the embodiments of the apparatus, system, and method, as represented in FIGS. 1 through 28, is not intended to limit the scope of the invention, as claimed, but is merely representative exemplary of exemplary embodiments of the invention.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments.

While the various aspects of the embodiments are presented in drawings, the drawings are not necessarily drawn to scale unless specifically indicated.

Figure 1:
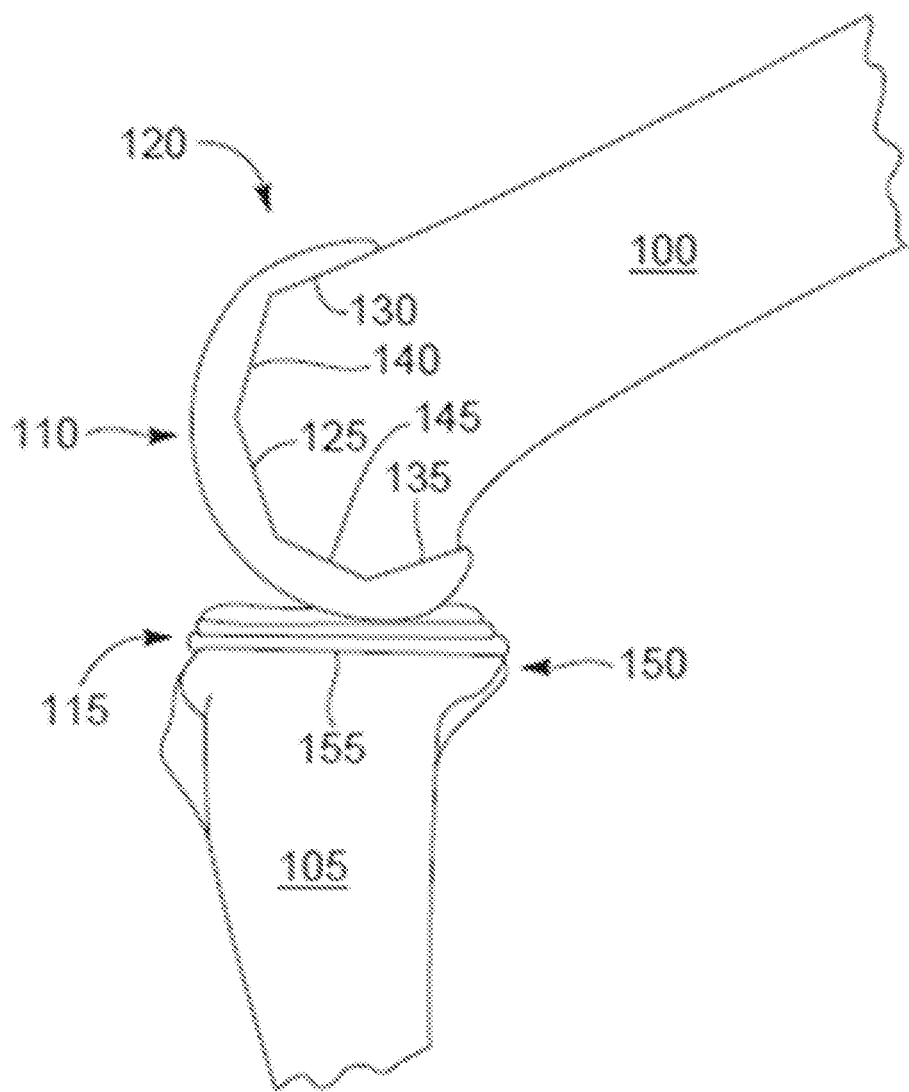
FIG. 1 is a side elevation view of a total knee arthroplasty according to one embodiment of the invention.

Referring to FIG. 1, a side elevation view illustrates an exemplary total knee arthroplasty according to one embodiment of the invention. While there are many techniques for performing knee arthroplasty, the procedure often includes moving the knee cap to one side of the joint to expose the distal end of the femur and the proximal end of the tibia. The femur 100 and the tibia 105 may then be cut and shaped to respectively receive a femoral arthroplasty prosthesis 110 and a tibial arthroplasty prosthesis 115.

In this example, FIG. 1 shows the femur's distal end 120 can be cut to provide a flat distal surface 125, which is generally cut at a range from four to six degrees of valgus from the femur's anatomic axis (not illustrated). Additionally, FIG. 1 shows the femur's distal end 120 can also be cut to have a flat anterior surface 130 and a flat posterior surface 135. Moreover, FIG. 1 shows the femur's distal end 120 can also be cut to include a flat anterior chamfer 140 surface, which is disposed between the flat anterior surface 130 and the flat distal surface 125, and a flat posterior chamfer surface 145, which is disposed between the flat posterior surface 135 and the flat distal surface 125.

Additionally, FIG. 1 shows that in some TKR procedures, a flat cut is made across the proximal end 150 of the tibia 105 to provide a flat proximal tibial surface 155. Depending on the design of the prosthesis that will be used, this cut is sometimes flat (perpendicular to the long axis) or is alternatively cut with a few degrees of posterior slope to match the knee's individual anatomy.

After the femur 100 and tibia 105 in the preceding example have been cut, FIG. 1 shows that femoral arthroplasty prosthesis 110 and the tibial arthroplasty prosthesis 115 can be placed on the bones to ensure both that bones have been cut to the proper dimensions and that the knee can function properly with the trial components. The tibial arthroplasty prosthesis 115 may be of any type known in the art, including "fixed bearing" and "mobile bearing" types. Thus, the tibial arthroplasty prosthesis may have articulating surfaces that are formed as a separate piece (for example, from polyethylene or a similar plastic) from the remainder of the tibial arthroplasty prosthesis 115, and are attached to the remainder of the tibial arthroplasty prosthesis through the use of any of a number of attachment technologies. The present invention is not limited to use with a certain type of tibial arthroplasty prosthesis, but may instead be used with any of a wide variety of tibial arthroplasty prostheses marketed by various manufacturers.

One of the primary goals in knee arthroplasty is to balance the gap between the cut surfaces of the femur and the tibia so that the gap between the surfaces, which is typically between about 8 and about 15 millimeters ("mm"), is the same when the joint is flexed (meaning the knee is bent) as when the joint is extended (meaning the leg is straightened). When these flexion/extension gaps are essentially the same size, the knee has essentially the same amount of play when the knee is flexed as it does when the knee is extended. Accordingly, balancing the flexion/extension gaps can help stabilize the knee and, thereby, provide a better chance of good clinical functioning, patient satisfaction, and component longevity.

Another primary goal in knee arthroplasty is to ensure that the knee is properly balanced from side to side so the knee does not have an excessive valgus (meaning a knock-kneed) or an excessive varus (meaning a bow-legged) configuration. Not only does balancing the knee's varus/valgus alignment provide the leg with a more aesthetically pleasing look, but this balancing also allows weight to be properly distributed across the articulating surfaces of the knee as it functions. As a result, balancing the knee's varus/valgus alignment can provide an even wear across prosthetic articulating surfaces, increase component longevity, and improve the patient's sense of stability through range of motion.

Often, balancing the knee's flexion/extension gaps and/or varus/valgus alignment can be difficult. For instances, if a portion of one or more surfaces on the femur and/or the tibia are missing due to prior mechanical injury, bone deformation, inaccurate cutting, damage that occurred when a primary component was removed for a revision knee surgery, or some other factor, then the knee's flexion/extension gaps and/or the varus/valgus alignment may become imbalanced and prevent the knee from functioning properly. When the knee's flexion/extension gaps and/or varus/valgus alignment are not balanced, there are several conventional methods that can be used to balance the gaps and/or straighten the knee's alignment.

In one example, where the knee's flexion/extension gaps or varus/valgus alignment are unbalanced because too much bone is missing from a side of the femur and/or the tibia, the high side of the bone surface is removed to balance the knee and one or more thicker prosthetic components are often used to compensate for the missing bone. Unfortunately, the result is that healthy bone that could otherwise facilitate the secure attachment of the implant must be removed. Additionally, there is a chance that too much bone will be removed, resulting in an improper fit of the implant. Further, the process of resecting the bone may change the fit of the joint so that the joint spacing must again be corrected after the high side of the bone surface is removed.

In another example, where a missing portion of bone causes the knee's flexion/extension gaps and/or varus/valgus alignment to be unbalanced, a relatively large portion of the low end of the bone (or the portion missing desired bone) is removed with a step or slanted cut to allow a substantially square or large-wedged spacer to be placed between the bone and the prosthesis to properly balance the knee. These large augments are often attached to the prosthesis with screws, and typically begin at 4 mm heights. Furthermore, these large augments often fill an entire compartment (either medial or lateral) on either the tibial or femoral side of the knee. Again, the consequences may include removal of excessive healthy bone, improper fit with the implant, continued problems with the joint spacing.

In still another example, the ligaments and other soft tissue around the knee are cut and otherwise loosened on the tight side of the knee to balance the gaps and/or to balance the knee's alignment. This weakens the ligaments and may destabilize the knee. Furthermore over loosening may lead to the need for additional adjustments.

In yet another example, the low end of the bone is filled by adding cement between the low end of the bone and the prosthetic component that is attached to the bone. Unfortunately, the cement may tend to migrate from its ideal location before it hardens. Thus, it may be difficult to cause the cement to cure such that a proper implant support surface is formed. Pressure on the knee, as when the implant is seated on the implant surface, may cause the cement to squeeze out of the desired location.

Figure 2:
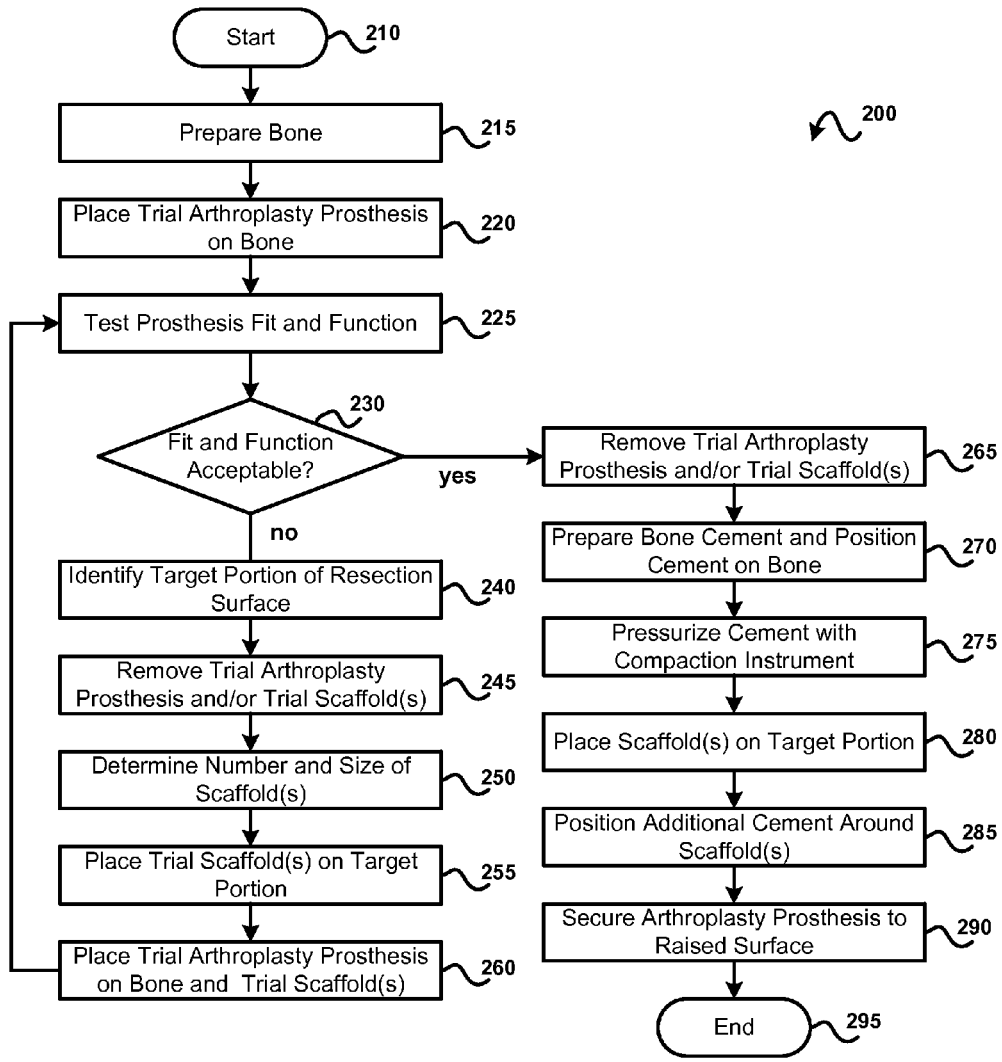
FIG. 2 is a flowchart diagram of a method of performing joint arthroplasty according to one embodiment of the invention.

Referring to FIG. 2, a flowchart diagram illustrates a method 200 of performing joint arthroplasty according to one embodiment of the invention. The method 200 may apply to any procedure in which any portion of an articulating surface is to be removed, including total arthroplasty, hemi-arthroplasty, unicompartmental arthroplasty, and the like. Furthermore, the method 200 may apply to a first-time arthroplasty, or to a procedure in which a previously-performed arthroplasty is to be revised. Yet further, the method 200 may apply to a wide variety of joints. Although the following description is focused on the knee, with reference to the exemplary anatomy and implants shown and described in FIG. 1, those of skill in the art will recognize that the present invention may also be used in connection with a wide variety of joint replacements including but not limited to knee, ankle, shoulder, and wrist replacements.

The method 200 may start 210 with a step 215 in which the bone is prepared for arthroplasty. This may require the prior performance of steps known in the art, such as making the necessary incisions to expose the bone, moving other tissues out of the way (such as the kneecap in the case of a knee arthroplasty), and/or applying one or more retractors to maintain access to the host bone. Preparation of the host bone may entail, in the case of a first-time arthroplasty, resection of the bone to remove one or more natural articular processes. In the case of a revision arthroplasty, preparation of the host bone may entail removal of the original prosthetic component(s) from the host bone and/or resection of the host bone to remove additional bone tissue. In any case, preparation of the host bone may result in the exposure of a resection surface.

Once the bone has been prepared, the method 200 may proceed to a step 220 in which a trial arthroplasty prosthesis is placed on the resection surface of the bone. The trial arthroplasty prosthesis may be similar in shape to the actual arthroplasty prosthesis to be implanted on the bone (for example, the tibial arthroplasty prosthesis 115 of FIG. 1), except that the trial arthroplasty prosthesis may lack anchoring stems, bony in-growth surfaces, or other attachment features possessed by the tibial arthroplasty prosthesis 115. Thus, the trial arthroplasty prosthesis may be easy to place on the host bone for temporary purposes, and may provide a suitable approximation of the manner in which the actual arthroplasty prosthesis would perform with the existing support provided by the host bone.

With the trial arthroplasty prosthesis in place, the method 200 may proceed to a step 225 in which the fit and function of the trial arthroplasty prosthesis are tested. Because the trial arthroplasty prosthesis may be similar to the actual arthroplasty prosthesis, this testing may provide an indication of the manner in which the actual arthroplasty prosthesis will function if implanted without further modifications.

This fit and function testing may be carried out through a variety of methods known in the art. For example, the surgeon may move the joint through its range of motion, examine the joint space to determine the amount of space between the various articulating surfaces at one or more relative positions within the range of motion of the joint, and/or move the joint in directions in which it is generally not intended to move to assess the amount of play in the joint. In the case of a knee replacement, fit and function texting may entail testing the joint to assess flexion/extension gaps and/or varus/valgus alignment. If desired, fit, alignment, and/or function of the joint may be evaluated through the use of various computer navigation and/or joint motion verification systems.

The fit and function testing may indicate that the fit and function are proper. Thus, in response to a query 230, the trial arthroplasty prosthesis may be replaced with the actual prosthesis, and if no further alterations are made to the host bone, the adjoining bone, or the ligaments in the joint, the joint may be expected to operate properly. In such an event, the method 200 may proceed to a step 265 in which preparations will be made to implant the actual arthroplasty prosthesis. The step 265 and the following steps will be set forth in further detail subsequently.

The fit and function testing may alternatively reveal that one or more aspects of the joint will need to be adjusted to ensure proper operation prior to implantation of the actual arthroplasty prosthesis. Thus, in response to the query 230, the method 200 may proceed to a step 240 in which a target portion of the resection surface is identified. The target portion may be visibly recessed by comparison with a non-target portion of the resection surface. Alternatively, the target portion may not have a visible recess, but may simply be recessed by comparison with a theoretical surface on which the actual arthroplasty prosthesis is to rest to provide proper fit and function. The fit and function testing may provide a recommended position or position change for the actual arthroplasty prosthesis, which may lead to a determination of a portion of the resection surface that is to be elevated. In the event that computer navigation or joint evaluation systems are used, such systems may directly indicate the desired position of the actual arthroplasty prosthesis and/or the target surface of bone to be elevated. One example of a target portion of a resection surface will be shown in connection with FIG. 3, as follows.

Figure 3:
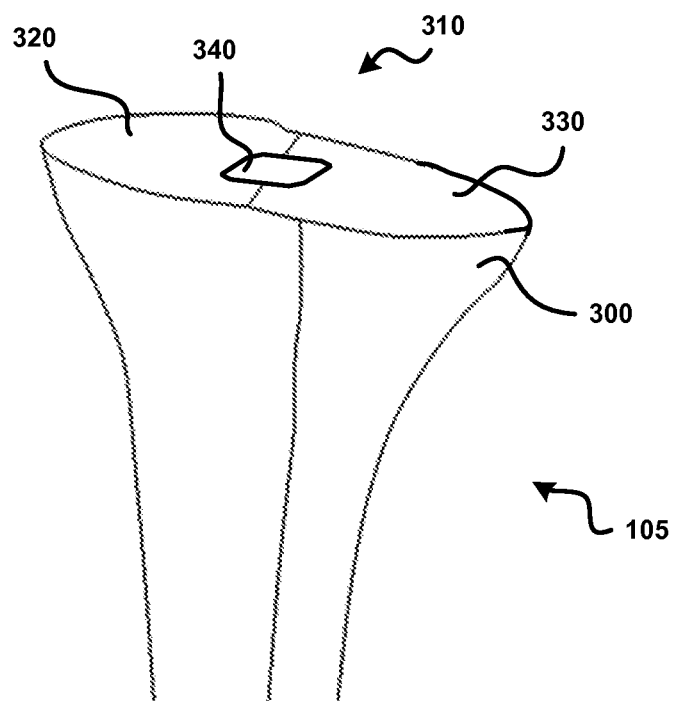
FIG. 3 is a perspective view illustrating a tibial plateau after resection, with a target portion defined by the resection surface.

Referring to FIG. 3, a perspective view illustrates a tibial plateau after resection, with a target portion defined by the resection surface. More specifically, the tibia 105 of FIG. 1 may have a proximal end with a tibial plateau 300 on which a resection surface 310 is disposed. As mentioned previously, the resection surface 310 may be formed as part of the current surgical operation, in which the natural articulating surfaces are removed, or in the case of revision surgery, the resection surface 310 may remain after removal of one or more arthroplasty implants that were implanted in a previous arthroplasty procedure.

Through the aid of the present invention, the resection surface 310 may be non-uniformly built up in such a manner that it can support the actual arthroplasty prosthesis at the desired position and orientation. The resection surface 310 may thus have a baseline portion 320 that is already at the proper height and/or orientation to support the actual arthroplasty prosthesis, and a target portion 330 that is to be built up more than the remainder of the resection surface 310, i.e., higher than the baseline portion 320. The target portion 330 may be recessed relative to the baseline portion 320 as shown in FIG. 3. In such an event, the target portion 330 may be formed by, for example, making a preliminary planar resection in the tibia 105, and then making a second planar resection at an angle to the preliminary planar resection to remove a region of poor quality bone or the like.

In alternative embodiments, the target portion 330 may not be lower than the baseline portion. The target portion 330 may simply represent a region of the resection surface 310 that is to receive additional cement in order to build up the target portion 330 to a greater height in order to cooperate with the baseline portion 320 to support the actual arthroplasty prosthesis in the desired position and/or orientation.

The resection surface 310 may have a hole 340 that accommodates a stem of the tibial arthroplasty prosthesis 115. The hole may be 340 may remain from a previous joint arthroplasty procedure (in the case of revision arthroplasty), may be formed immediately after the resection surface 310, or may be formed in a subsequent step. It may be desirable to form the hole 340 in a subsequent step because the optimal position and/or orientation for the hole 340 may depend upon the final position and/or orientation of the tibial arthroplasty prosthesis 115. Hence, it may be desirable to form the hole 340 after the target portion 330 of the resection surface 310 has been built up in subsequent steps.

Returning to FIG. 2, once the target portion 330 has been identified, the method 200 may proceed to a step 245 in which the trial arthroplasty prosthesis and/or any trial scaffolds present on the resection surface 310 are removed from the resection surface 310. Then, in a step 250, the surgeon may determine the likely number and/or size of scaffolds to be applied to the target portion 330 in order to correct the deficiency or deficiencies observed in the step 225. This may be done, for example, by using pre-established formulas, charts, or tables, or by simply estimating based on the magnitude of the deficiency observed in the fit and function testing. In a step 255, the selected trial scaffold(s) may be placed on the target portion 330.

Figure 4:
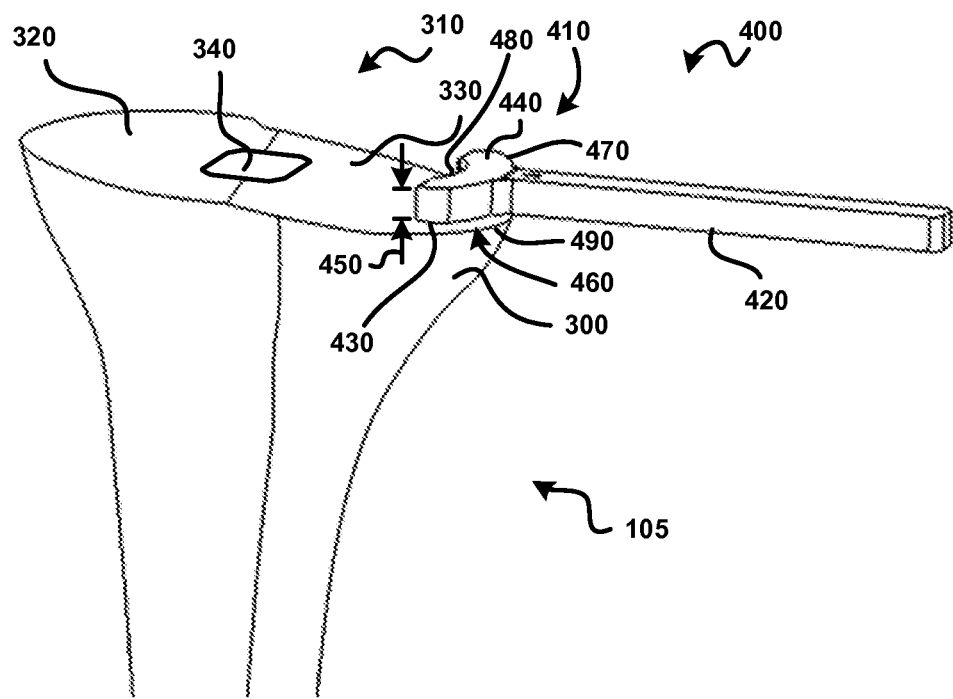
FIG. 4 is a perspective view illustrating placement of a trial scaffold on the target portion of the resection surface.

Referring to FIG. 4, a perspective view illustrates placement of a trial scaffold 400 on the target portion 330 of the resection surface 310. The trial scaffold 400 may have a main body 410 and a handle 420 connected to the main body. The main body 410 may have a shape that approximates that of a scaffold, as will be shown and described subsequently. Thus, the main body 410 may have a bone-facing trial surface 430 and a joint-facing trial surface 440, which may optionally be parallel to each other as shown to provide a thickness 450 that is substantially uniform across the bone-facing trial surface 430 and across the joint-facing trial surface 440.

If desired, the joint-facing trial surface 440 may instead be angled relative to the bone-facing trial surface 430. For example, the main body 410 may be thicker toward the exterior edge of the tibial plateau 300 so that the joint-facing trial surface 440 is substantially parallel to the baseline portion 320 of the resection surface 310. Alternatively, the joint-facing trial surface 440 may be angled relative to the bone-facing trial surface 430 in a variety of different ways, as needed to compensate for the particular defect discovered in the fit and function testing. Thus, the joint-facing trial surface 440 may be angled medially, laterally, anteriorly, posteriorly, or any combination thereof relative to the bone-facing trial surface 430.

The bone-facing trial surface 430 and the joint-facing trial surface 440 may cooperate to define an exterior trial scaffold wall 460. The exterior trial scaffold wall 460 may have a curved shape with a convex portion 470 and a concave portion 480. The concave portion 480 may be positioned on the opposite side of the exterior trial scaffold wall 460 from the convex portion 470, providing the main body 410 with a kidney shape. The convex portion 470 may have shape matched to that of a convex portion 490 of the resection surface 310. The concave portion 480 may be oriented toward the hole 340.

FIG. 4 is merely exemplary. In alternative embodiments, multiple trial scaffolds (not shown) may be used. Such trial scaffolds may be stacked on top of each other, aligned end-to-end, and/or otherwise positioned to approximate the position of the proposed scaffold(s). Trial scaffolds having a wide variety of shapes may be used to approximate corresponding differently-shaped scaffolds.

Returning to FIG. 2, once the trial scaffold 400 has been placed on the target portion 330, the method 200 may proceed to a step 260. In the step 260, a trial arthroplasty prosthesis 500 may be placed on the resection surface 310 and the trial scaffold 400.

Figure 5:
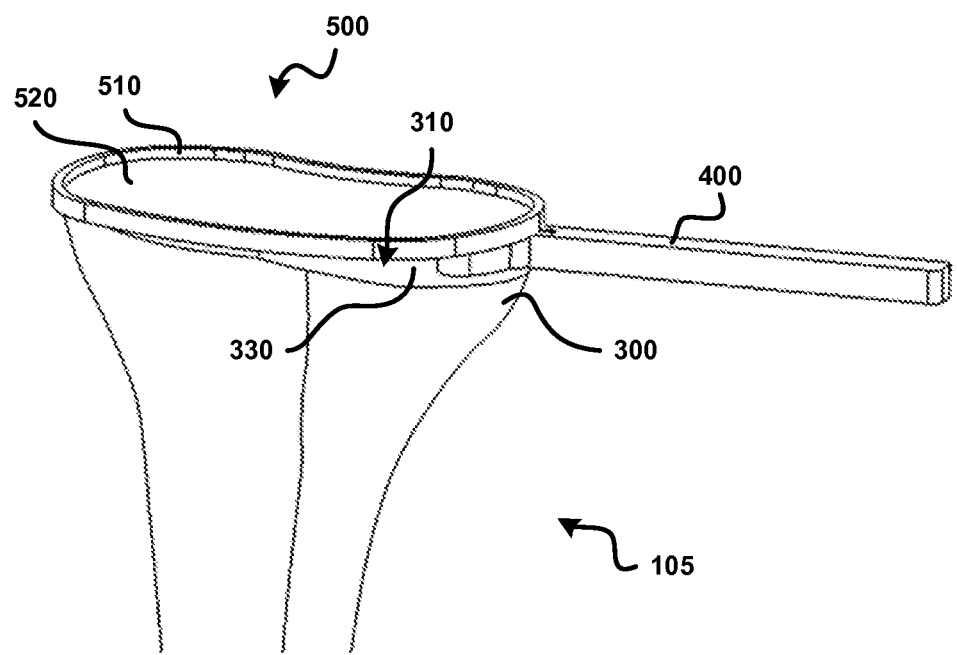
FIG. 5 is a perspective view illustrating placement of a trial arthroplasty prosthesis on the resection surface and the trial scaffold.

Referring to FIG. 5, a perspective view illustrates placement of the trial arthroplasty prosthesis 500 on the resection surface 310 and the trial scaffold 400, which was placed on the resection surface 310 in FIG. 4. The trial arthroplasty prosthesis 500 may have an exterior wall 510 and a base plate 520 as shown, and may also have one or more articulating surfaces (not shown) that are similar in size and shape to those of the tibial arthroplasty prosthesis 115. If desired, the articulating surfaces may be provided on a separate piece that attaches to the base plate 520, either fixedly or movably depending on the type of tibial arthroplasty prosthesis to be implanted. The base plate 520 may be positioned to rest on the baseline portion 320 of the resection surface 310 and on the joint-facing trial surface 440 of the trial scaffold 400. Thus, the trial arthroplasty prosthesis 500 may provide a reasonable approximation of the location and function of the tibial arthroplasty prosthesis 115.

Returning to FIG. 2, once the step 260 has been performed, the trial arthroplasty prosthesis may be in position for further fit and function testing. Thus, the method 200 may then return to the step 225, in which the fit and function of the joint are tested, with the trial arthroplasty prosthesis in place. The method 200 may again perform the query 230. If any deficiency remains in the fit and function, the method 200 may again proceed to the step 240. However, since the target portion 330 may have already been identified in the previous performance of the step 240, the method 200 may skip the step 240 and proceed directly to the step 245 in which the trial arthroplasty prosthesis and the trial scaffold(s) are removed. Then, the step 250, the step 255, and the step 260 may again be performed, with the number and or size of the scaffold(s) adjusted to correct the deficiency observed in the step 225. Fit and function testing may again be performed in the step 225, followed by the query 230. This cycle may be repeated as long as fit and function testing do not provide satisfactory results.

Once fit and function are satisfactory, it may be assumed that the scaffold(s) that correspond to the trial scaffolds (or the trial scaffold 400 in the example of FIG. 4) have the necessary size, shape, and/or placement of the scaffold(s) to provide proper joint operation. The method 200 may thus proceed to a step 265 in which the trial scaffold 400 and the trial arthroplasty prosthesis 500 are removed from the resection surface 310. Then, in a step 270, the bone cement may be prepared and positioned on the resection surface 310. The bone cement may then be pressurized, in a step 275, with a pressurization instrument such as that disclosed in U.S. patent application Ser. No. 13/032,386, which is incorporated herein by reference. The compaction instrument may be used to fill voids and/or holes in the tibia 105 to help the bone cement that will subsequently be applied to the target portion 330 to remain in place. As part of this process, the bone cement may be inserted into and/or pressurized within the hole 340. The bone cement may also be placed on the target portion 330, under the location at which the scaffold is to be placed, to facilitate full encapsulation of the scaffold by the cement. In the alternative to the foregoing, the step 270 and the step 275 may be omitted, and all of the bone cement may be applied after the scaffold has been placed.

If desired, the specific location on the target portion 330 that is to receive a scaffold 600 may be prepared to securely retain the scaffold 600 during the subsequent cementing steps. As will be shown and described subsequently, the scaffold 600 may have bone penetrating features that protrude into the bone of the target portion 330 to anchor the scaffold in place 600. If desired, holes or indentations (not shown) may be formed in the target portion 330 through the use of a punch or other tool in order to prepare the target portion 330 to securely receive the scaffold 600. Such preparation may be particularly advantageous if the target portion 330 has sclerotic or other hard bone that could be difficult for the bone penetrating features of the scaffold 600 to break through on their own. Once the target portion 330 of the resection surface 310 has been properly prepared, the method 200 may proceed to a step 280 in which the scaffold 600 is placed on the target portion 330. Exemplary placement of the scaffold 600 will be shown and described in connection with FIG. 6.

Figure 6:
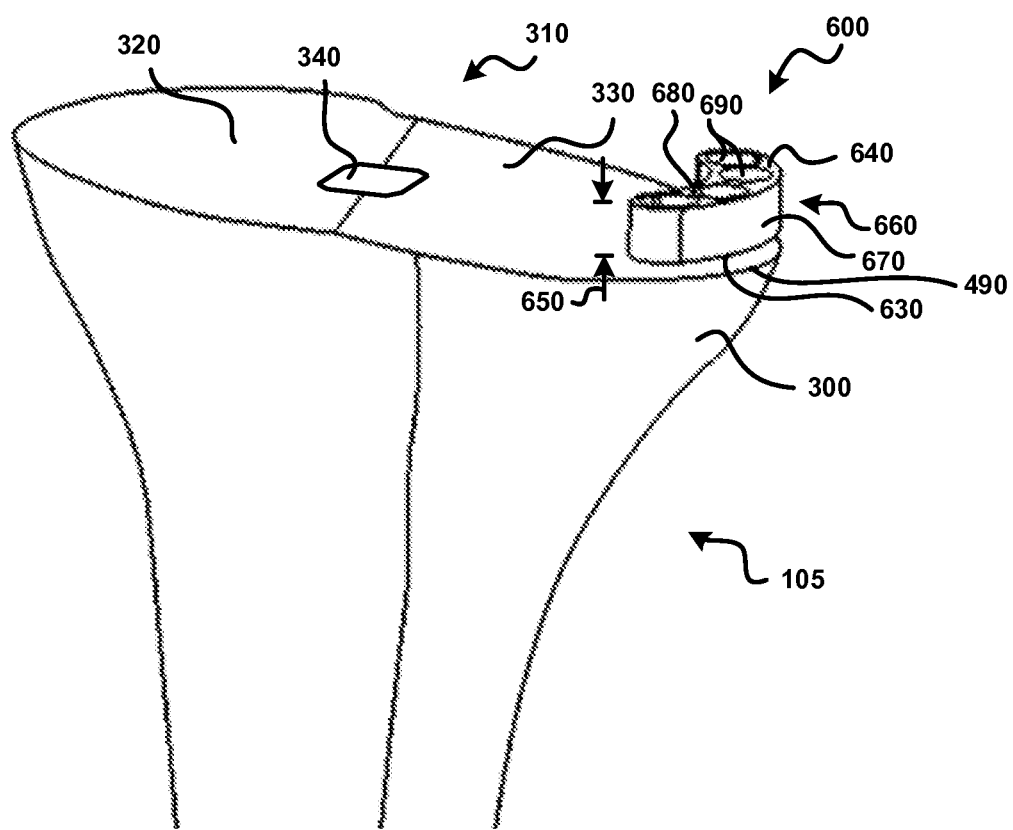
FIG. 6 is a perspective view illustrating placement of a scaffold on the target portion of the resection surface.

Referring to FIG. 6, a perspective view illustrates placement of the scaffold 600 on the target portion 330 of the resection surface 310. FIG. 6 does not show the presence of any bone cement; however, if the step 270 and/or the step 275 were carried out as set forth above, bone cement may be present on the target portion 330, in the hole 340, or on the baseline portion 320 of the resection surface 310.

As shown, the scaffold 600 may have a shape similar to that of the trial scaffold 400. Thus, the scaffold 600 may have a bone-facing surface 630 and a joint-facing surface 640, which may optionally be parallel to each other as shown to provide a thickness 650 that is substantially uniform across the bone-facing surface 630 and across the joint-facing surface 640.

If desired, the joint-facing surface 640 may instead be angled relative to the bone-facing surface 630. For example, as described in connection with the trial scaffold 400, the scaffold 600 may be thicker toward the exterior edge of the tibial plateau 300 so that the joint-facing surface 640 is substantially parallel to the baseline portion 320 of the resection surface 310. Alternatively, the joint-facing surface 640 may be angled relative to the bone-facing surface 630 in a variety of different ways, as needed to compensate for the particular defect discovered in the fit and function testing. Thus, the joint-facing surface 640 may be angled medially, laterally, anteriorly, posteriorly, or any combination thereof relative to the bone-facing surface 630.

The bone-facing surface 630 and the joint-facing surface 640 may cooperate to define an exterior scaffold wall 660. The exterior scaffold wall 660 may have a curved shape with a convex portion 670 and a concave portion 680. The concave portion 680 may be positioned on the opposite side of the exterior scaffold wall 660 from the convex portion 670, providing the scaffold 600 with a kidney shape. Like the convex portion 470 of the exterior trial scaffold wall 460 of the trial scaffold 400, the convex portion 670 of the exterior scaffold wall 660 may have shape matched to that of the convex portion 490 of the resection surface 310. The concave portion 680 may be oriented toward the hole 340.

The concave portion 680 may provide distance between the scaffold 600 and the hole 340 to help the scaffold 600 avoid interference with anchoring of the tibial arthroplasty prosthesis 115 in the hole 340. The convex portion 670 may follow the curvature of the convex portion 490, which may cause the bone-facing surface 630 to lie on the stronger cortical bone at the periphery of the resection surface 310, rather than on the weaker and more porous cancellous bone on the interior of the resection surface 310. Placing the scaffold 600 on cortical bone may reduce the likelihood that the scaffold 600 will be pressed distally into the bone tissue of the tibia 105 during subsequent steps such as further cement compaction, placement of the tibial arthroplasty prosthesis 115, and re-assembly of the joint.

The scaffold 600 may also have an aperture system including one or more apertures that extend from the bone-facing surface 630 to the joint-facing surface 640. In the example of FIG. 6, the aperture system may include a plurality of apertures 690. The apertures 690 may beneficially be relatively large so that bone cement is able to flow through them, thus providing bone cement columns through the scaffold 600 that directly support the tibial arthroplasty prosthesis 115 on the target portion 330 of the resection surface 310.

In fact, when viewed from a direction perpendicular to the joint-facing surface 640, the apertures 690, together, may have an area of at least half that of the joint-facing surface 640 that exists outside the apertures 690. Further, the apertures 690, together, may have an area of at last three quarters of that of the joint-facing surface 640 that exists outside the apertures 690. Still further, the apertures 690, together, may have an area at least equal to that of the joint-facing surface 640 that exists outside the apertures 690. Thus, in effect, the scaffold 600 may be more hole than solid material. This may cause the bone cement extending through the apertures 690 to bear more of the load between the tibial arthroplasty prosthesis 115 and the tibia 105 than the scaffold 600. In alternative embodiments (not shown), the apertures may, together, have an area greater than that of the bone-facing surface that exists outside the apertures, by a ratio of 1.25:1, 1.5:1, 1.75:1, or even 2:1.

The scaffold 600 may remain in place after implantation of the tibial arthroplasty prosthesis 115. However, the bone cement columns extending through the apertures 690, rather than the scaffold 600, may bear the loading of the tibial arthroplasty prosthesis 115 on the tibia 105. Thus, the scaffold 600 need not be formed of a material having high compressive strength. In some embodiments, the scaffold 600 may be formed of PEEK or a similar material. If desired, the scaffold 600 may be formed of a bio-absorbable material. In some embodiments, the scaffold 600 may be custom-made for the particular surgery for which it will be used. For example, the surgeon may enter the desired dimensions of the scaffold 600 into a 3D printer, which may produce the scaffold 600 according to the specifications provided.

Returning to FIG. 2, after the scaffold 600 has been placed on the target portion 330 of the resection surface 310, the method 200 may proceed to a step 285 in which additional cement is positioned in and around the scaffold 600. This step will be shown and described in connection with FIG. 7, as follows.

Figure 7:
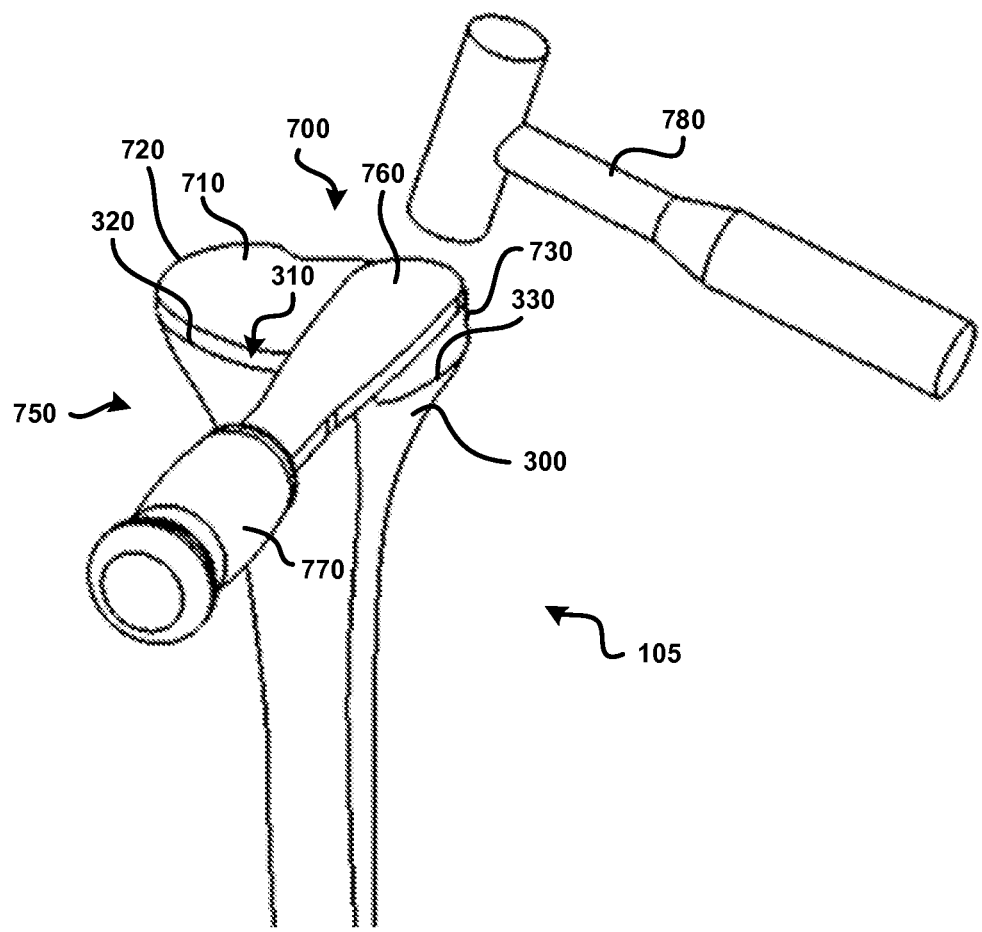
FIG. 7 is a perspective view illustrating placement of bone cement on the target portion of the resection surface, around the scaffold.

Referring to FIG. 7, a perspective view illustrates placement of bone cement 700 on the target portion 330 of the resection surface 310, around the scaffold 600. As shown, the bone cement may have a raised surface 710, which may be substantially flat so as to accommodate the shape of the adjoining portion of the tibial arthroplasty prosthesis 115. The raised surface 710 may be angled to position the tibial arthroplasty prosthesis 115 to provide optimal functionality of the knee joint. The bone cement 700 may have a baseline portion 720 positioned on the baseline portion 320 of the resection surface 310, and a target portion 730 positioned on the target portion 330 of the resection surface 310.

As indicated previously, it may be advantageous to urge the bone cement 700, under pressure, into the resection surface 310 prior to placement of the scaffold 600. This may be done through the use of a tool 750, which may have a flat blade 760 suitable for cement contact and a handle 770 that can be gripped by the surgeon and/or other tools known in the art. This pressurization can be performed, for example, as shown in FIG. 7 (but prior to the placement of the scaffold 600 and the full quantity of bone cement 700 shown in FIG. 7) by positioning the flat blade 760 over the bone cement 700 on the resection surface 310, and then striking the flat blade 760 with a compaction tool 780 such as a mallet to generate force to drive the bone cement 700 downward into the porous bone of the resection surface 310 and particularly, the cancellous bone toward the center of the resection surface 310. This step may be desirable because, once the scaffold 600 is in place, it may impede access of the flat blade 760 to the resection surface 310 and reduce the pressure that can be applied to the bone cement 700.

After the bone cement 700 is pressurized into the resection surface 310, the scaffold 600 may be placed as shown and described previously in connection with FIG. 6. The bone cement 700 may then be placed on, around, and/or through the scaffold 600 as well as across the remainder of the resection surface 310, in preparation for implantation of the tibial arthroplasty prosthesis 115. This may be done through the use of the tool 750 and/or the compaction tool 780. The tibial arthroplasty prosthesis 115 may further drive the bone cement 700 into the porous bone of the resection surface 310 when it is pounded or otherwise driven into place. Firm securement of the scaffold 600 to the target portion 330 of the resection surface 310 may be accomplished via penetration of the bone of the resection surface 310 with bone penetrating features of the scaffold 600, which will be shown and described subsequently. This may help keep the scaffold 600 from being dislodged during the subsequent steps in which the tibial arthroplasty prosthesis 115 will be placed, driven, and/or impacted.

Returning to FIG. 2, once the bone cement 700 has been placed, the step 285 may be complete. The raised surface 710 may be ready for placement of the tibial arthroplasty prosthesis 115. The raised surface 710 will be further shown and described in connection with FIG. 8.

Figure 8:
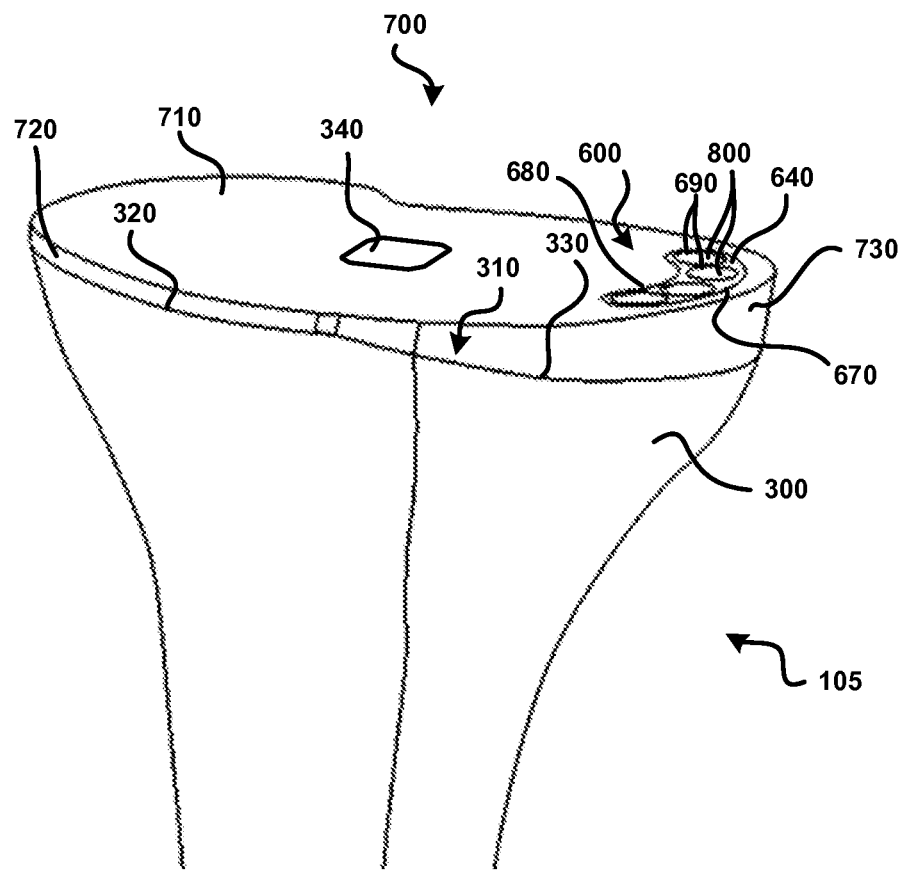
FIG. 8 is a perspective view illustrating a raised surface that may be defined by the curing bone cement after addition of the bone cement on the target portion of the resection surface around the scaffold, thus elevating the surface upon which the arthroplasty prosthesis will rest.

Referring to FIG. 8, a perspective view illustrates the raised surface 710 that may be defined as the bone cement 700 cures after addition of the bone cement 700 on the target portion 330 of the resection surface 310 around the scaffold 600, thus elevating the surface upon which the arthroplasty prosthesis will rest. Notably, the tibial arthroplasty prosthesis 115 may be placed on the raised surface 710 before the raised surface 710 cures. Thus, the raised surface 710 represented in FIG. 8 may not yet be fully cured. However, the height of the raised surface 710 over the target portion 330 of the resection surface 310 may be determined by the location of the joint-facing surface 640 of the scaffold 600. Thus, with the scaffold 600 in place, the position and orientation at which the tibial arthroplasty prosthesis 115 will rest on the raised surface 710 may be accurately established in spite of the fact that the raised surface 710 has not yet hardened.

As mentioned previously, the raised surface 710 may have a generally planar shape. The bone cement 700 may also be generally flush with the scaffold 600 so that the raised surface 710 is substantially coplanar with the joint-facing surface 640 of the scaffold 600. In the example of FIG. 8, the scaffold 600 may be positioned proximate the medial edge of the target portion 730 of the bone cement 700. In alternative embodiments, the resection surface 310 may have a differently-located target portion, and the scaffold 600 (or a differently-configured scaffold), may be positioned on the differently-located target portion. As also mentioned previously, placing the scaffold 600 proximate the periphery of the resection surface 310 may advantageously enable the scaffold 600 to rest on cortical bone, but in some embodiments, it may be desirable to position the scaffold 600 (or a differently-configured scaffold) interior to the periphery of the resection surface 310.

During the performance of the step 285, the bone cement may be inserted into and/or compacted within the apertures 690 of the scaffold 600. The curing bone cement 700 may form a cement column 800 within each of the apertures 690. The cement columns 800 may also extend to a height flush with the joint-facing surface 640 of the scaffold 600, and may thus be positioned to receive loading between the tibial arthroplasty prosthesis 115 and the tibia 105. It may be advantageous to form the hole 340 at this stage, once the raised surface 710 has been formed and the optimal position and/or orientation for the hole 340 can be determined.

Returning to FIG. 2, after completion of the step 285, the method 200 may proceed to a step 290 in which the actual arthroplasty prosthesis, or the tibial arthroplasty prosthesis 115, in the example of FIG. 1, is placed on the raised surface 710 of the bone cement 700. This may be done before the bone cement 700 has fully cured. Thus, upon curing, the bone cement 700 may adhere to the tibial arthroplasty prosthesis 115 to keep the tibial arthroplasty prosthesis 115 securely in place on the raised surface 710. IF desired, extra bone cement 700 may be placed on the raised surface 710 and/or on one or more bone-facing surfaces of the tibial arthroplasty prosthesis 115 prior to placement of the tibial arthroplasty prosthesis 115 on the raised surface 710, to ensure that thorough contact exists between the tibial arthroplasty prosthesis 115 and the bone cement 700. The placement of the tibial arthroplasty prosthesis 115 will be further shown and described in connection with FIG. 9.

Figure 9:
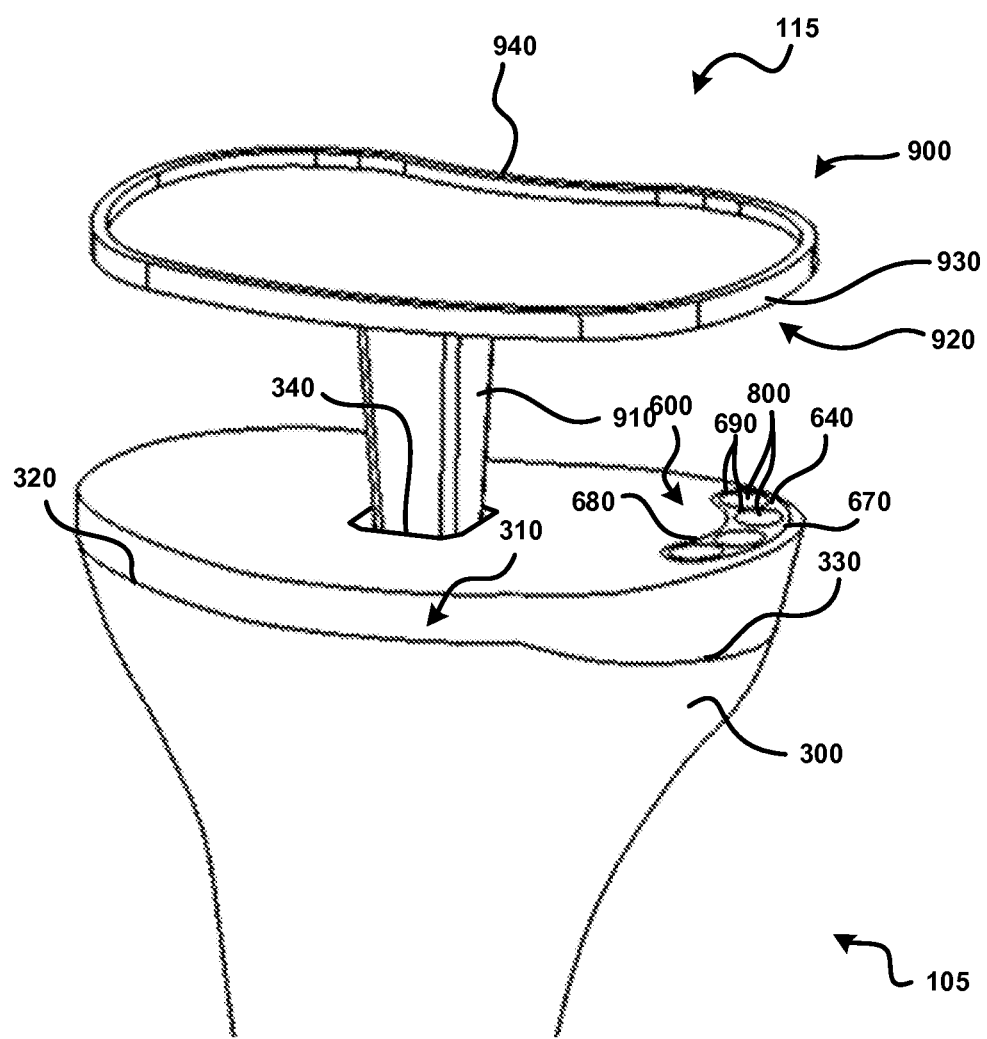
FIG. 9 is a perspective view illustrating placement of a tibial arthroplasty prosthesis on the raised surface.

Referring to FIG. 9, a perspective view illustrates placement of the tibial arthroplasty prosthesis 115 on the raised surface 710 of the bone cement 700 and on the cement columns 800 within the apertures 690 of the scaffold 600. As shown, the tibial arthroplasty prosthesis 115 may have a tibial tray 900 and a stem 910. The tibial tray 900 may be substantially the same size and shape as the trial arthroplasty prosthesis 500. The stem 910 may be inserted into the hole 340.

The tibial tray 900 may have an exterior prosthesis wall 920 with a shape that is generally matched to the shape of the raised surface 710. The raised surface 710, in turn, may have a shape that is matched to that of the resection surface 310. The exterior prosthesis wall 920 may have a convex curvature 930 that matches the curvature of the convex portion 490 of the resection surface 310 and/or the convex portion 670 of the exterior scaffold wall 660 of the scaffold 600. Furthermore, the exterior prosthesis wall 920 may have a concave curvature 940 aligned with corresponding concave curvatures of the raised surface 710 and/or the resection surface 310.

The tibial tray 900 is shown without articulating surfaces. As with the trial arthroplasty prosthesis 500, the articulating surfaces of the tibial arthroplasty prosthesis 115 may be a separate piece from the tibial tray 900, and may be fixedly or movably attached to the tibial tray 900, depending on the type of the tibial arthroplasty prosthesis 115.

If desired, the joint-facing surface 640 of the scaffold 600, and thence, the raised surface 710 of the bone cement 700, may be positioned slightly higher than the desired final resting place of the tibial arthroplasty prosthesis 115. Then, after the tibial arthroplasty prosthesis 115 has been placed on the raised surface 710, but before the bone cement 700 has fully cured, the tibial arthroplasty prosthesis 115 may be urged toward the tibia 105 to pressurize the bone cement 700 into the bone of the resection surface 310 and/or the hole 340 and/or fill any remaining voids in the bone cement 700 adjacent to the tibial arthroplasty prosthesis 115. As the tibial arthroplasty prosthesis is driven toward the tibia 105, excess bone cement may be extruded out from between the resection surface 310 and the tibial arthroplasty prosthesis 115. The excess bone cement 700 may be removed with appropriate instruments and techniques well known in the art.

This may result in the raised surface 710 being positioned at its desired height relative to the tibia 105 such that the tibial arthroplasty prosthesis 115 is located in its final position relative to the tibia 105. The tibial arthroplasty prosthesis 115 may rest on a mantle of bone cement 700, which may be relatively narrower at the baseline portion 720 and thicker at the target portion 730. This mantle of bone cement 700 may quickly cure into a solid weight-bearing foundation for the tibial arthroplasty prosthesis 115 and may have substantially full surface area contact with the underside of the tibial arthroplasty prosthesis 115 to allow for secure fixation.

Returning to FIG. 2, once the step 290 is complete, the method 200 may end 295. Prior to the end 295, the joint (for example, the knee) may be reassembled by placing the articulating surfaces of the tibial arthroplasty prosthesis 115 into engagement with the natural or prosthetic articulating surfaces on the femur 100, and moving the adjoining tissues, such as the kneecap, back into their proper positions. The surgical exposure may also be closed and the joint may be braced and/or otherwise positioned for optimal recovery.

The method 200 is only one of many methods that may be used within the scope of the invention, in the alternative to the method 200 of FIG. 2. Additionally, a wide variety of arthroplasty prostheses, trial arthroplasty prostheses, scaffolds, compaction tools, trial scaffolds, and the like may be used in the alternative to those shown in FIGS. 3-9. Some alternatives will be shown and describe in connection with the following figures.

Figure 10:
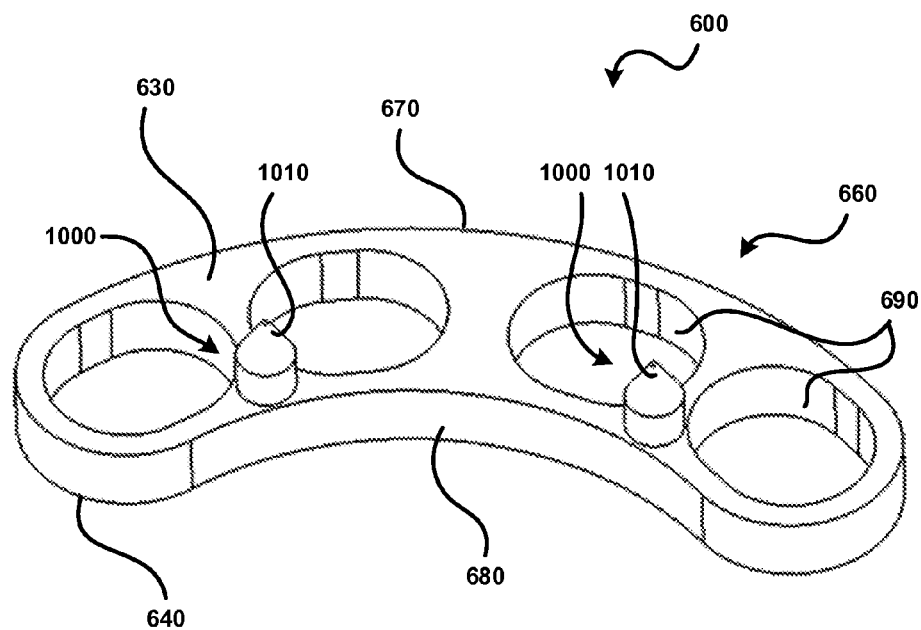
FIG. 10 is a perspective view illustrating the scaffold of FIGS. 6-9 in greater detail.

Referring to FIG. 10, a perspective view illustrates the scaffold 600 of FIGS. 6-9 in greater detail. FIG. 10 illustrates the scaffold 600 from a viewpoint facing the bone-facing surface 630. As shown, the bone-facing surface 630 may have bone penetrating features 1000 designed to penetrate the bone of the target portion 330 of the resection surface 310. As embodied in FIG. 10, the bone penetrating features 1000 may be spikes, each of which has a tip 1010 shaped to penetrate bone. The bone penetrating features 1000 may help to register the scaffold 600 on the target portion 330 of the resection surface 310 to help the scaffold 600 stay in place during the following procedures such as application of and compaction of the bone cement 700.

In general terms, the scaffold 600 may be insertable between a resection surface such as the resection surface 310, and a prosthesis such as the tibial arthroplasty prosthesis 115, in a plurality of locations and/or orientations. The scaffold 600 may be usable for a primary (first time) joint replacement and/or a revision arthroplasty situation, in which the shape of the bone that remains after removal of the primary prosthetic components may be significantly different from the resection surface provided by resecting the native joint. In some instances, the scaffold 600 may be inserted between the bone and its corresponding prosthesis without requiring any additional cutting to be done to the bone. The scaffold 600 may be sized and shaped to fit between a variety of anatomically different bone and prosthesis types, including but not limited to knee, ankle, shoulder, and wrist replacements.

The cross sectional shape of the scaffold 600 may include any of a number of different geometries including but not limited to crescent shapes, kidney shapes, rectangular shapes, V-shapes, trapezoidal shapes, horseshoe shapes, triangle shapes, teardrop shapes, round shapes, oval shapes, I-shapes, combinations thereof, and other complex shapes. The scaffold 600 may have a length dimension and width dimension, each of which is parallel to the bone-facing surface 630 and may range from 1 millimeter to 50 millimeters, or more precisely, from 5 millimeters to 25 millimeters. The scaffold 600 may have a thickness perpendicular to the bone-facing surface 630 ranging from 0.5 millimeters to 15 millimeters, or more precisely, from 1 millimeter to 5 millimeters. The bone-facing surface 630 and the joint-facing surface 640 may be parallel to each other as shown in FIG. 10, or angled relative to each other. The angle between the bone-facing surface 630 and the joint-facing surface 640 may range from 0° to 30°. Additional scaffold embodiments are disclosed in FIGS. 1-8 and 12 of the U.S. patent application Ser. No. 13/032,386, which is incorporated herein by reference.

In order to accommodate the varying anatomies, prostheses, and arthroplasty situations that may be encountered, the scaffold 600 may be provided in various configurations. If desired, the scaffold 600 may be part of a kit of scaffolds encompassing significant dimensional variation. For example, each scaffold may have a thickness different from that of the other scaffolds. A kit of five scaffolds may have thicknesses of one, two, three, four, and five millimeters, respectively. Alternatively, a kit of five scaffolds may have angles between the bone-facing surface 630 and the joint-facing surface 640 of 0°, 7.5°, 15°, 22.5°, and 30°, respectively.

The scaffolds 600 may have apertures that are different from the apertures 690 and/or serve purposes different from that of the apertures 690, as set forth previously. For example, in alternative embodiments, apertures may allow for the host bone to grow therethrough and/or allow components of the prosthesis to pass therethrough. A combination of apertures of various shapes and/or sizes may be used, or the apertures may be uniform in shape and/or size. The apertures may be organized in rows or columns, or their locations may be more random. The apertures may also minimize the total surface area of the scaffold to maximize cement contact with the prosthesis.

In this application, an "aperture" includes any structure that provides passage through the thickness of a part. An aperture may be fully-bounded like the apertures 690 of the scaffold 600 of FIG. 10, and may thus form a closed shape such as a circle, oval, or the like. In alternative embodiments, apertures may be only partially-bounded by the material of the scaffold. A partially-bounded aperture may intersect an edge of the profile of the scaffold such that only the interior edges of the aperture are bounded by the material of the scaffold. Such partially-bounded apertures may be necessary to accommodate various bosses or extrusions that may exist on the mating arthroplasty prostheses, such as stems, keels, pegs, flanges, or the like.

In the alternative to the bone penetrating features 1000 of FIG. 10, a variety of different bone penetrating features, including but not limited to posts, pegs, spikes, or other projections, may exist along the bone-facing surface 630 to aid in the fixation of the scaffold 600 to the underlying host bone. These bone penetrating features may take on a number of different geometries including but not limited to: cylindrical posts with or without spiked tips, spade-tipped projections, V-shaped projections, flathead tip projections, and pyramidal spikes. Each scaffold 600 may have one or more such bone penetrating features. The bone penetrating features may be used to enhance the fixation of the scaffold 600 into the cortical and/or cancellous bone. The locations of the bone penetrating features may vary along the bone-facing surface 630 of the scaffold 600, and may advantageously be positioned to avoid interference with the apertures 690. The bone penetrating features may be arranged along the outer periphery of the bone-facing surface 630 and/or on the interior regions of the bone-facing surface 630.

In some alternative embodiments (not shown), each scaffold may have multiple bone penetrating features that encompass a variety of geometries. For example, it may be advantageous to have longer bone penetrating features along one edge of the scaffold, with shorter bone penetrating features along the opposing edge, or wider bone penetrating features on one edge with narrower bone penetrating features on the opposing edge. The geometry of each bone penetrating feature may be dictated by type of bone it is designed to penetrate, as various features may fixate better in the different bone types such as cancellous and cortical bone.

Additionally or alternatively, the bone-facing surface 630 of the scaffold 600 may have other features to improve fixation to the host bone and/or the bone cement 700. For example, the bone-facing surface 630 and/or the interior surfaces of the apertures 690 may be roughened to increase the frictional fit between the scaffold 600 and the host bone. The roughened surfaces may also provide additional locations for bony ingrowth to occur and/or additional locations for the bone cement 700 to adhere. The bone-facing surface 630 and/or the interior surfaces of the apertures 690 may also be coated with various materials that may promote bony ingrowth such as hydroxyapatite, titanium, or other porous coatings. Other surface treatments such as hydrophobic coatings, hydrophilic coatings, and antimicrobial coatings may provide additional benefits including reduced friction, resistance to bacteria and extended life.

The scaffold 600 may be constructed from a number of materials including but not limited to plastics such as polymethyl-methacrylate (PMMA), poly-ether-ether-ketone (PEEK), ultra-high molecular weight polyethylene (UHM-WPE). Additionally or alternatively, the scaffold 600 may be constructed from metals such as titanium, stainless steel, and cobalt chromium. Additionally or alternatively, the scaffold 600 may be constructed from ceramic materials such as cubic zirconia, or from composite materials.

Figure 11:
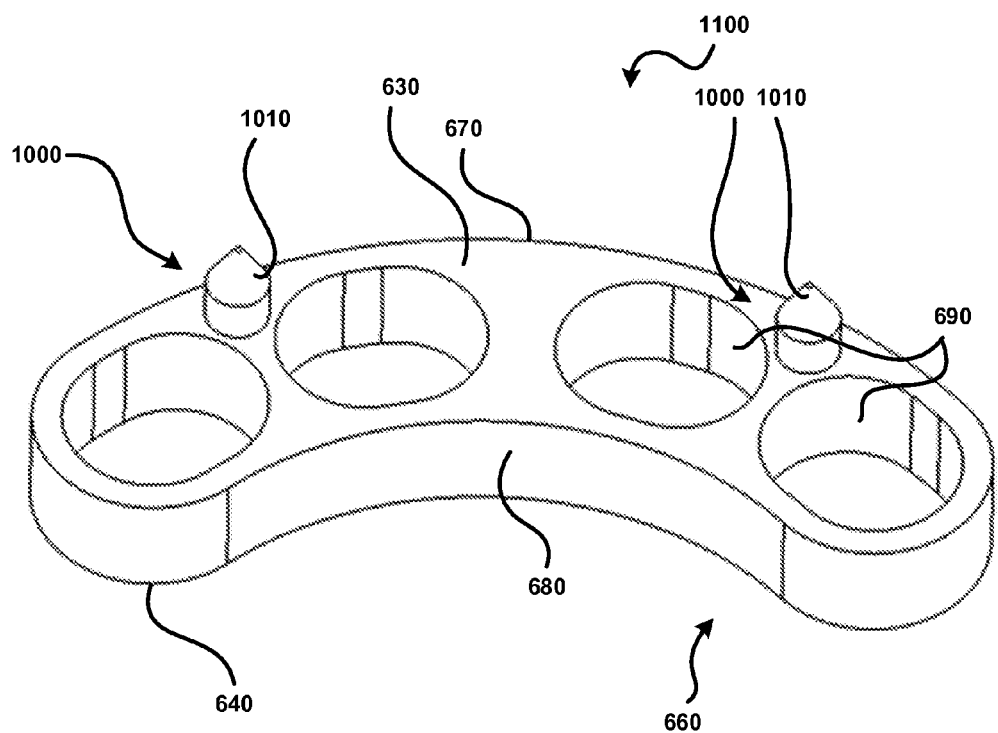
FIG. 11 is a perspective view illustrating a scaffold according to one alternative embodiment of the invention.

Referring to FIG. 11, a perspective view illustrates a scaffold 1100 according to one alternative embodiment of the invention. As shown, the scaffold 1100 may have a shape similar to that of the scaffold 600 of FIG. 10, except that the bone penetrating features 1000 may be positioned adjacent to the convex portion 670 of the exterior scaffold wall 660, rather than being positioned adjacent to the concave portion 680 of the exterior scaffold wall 660 as in FIG. 10. This may allow for the bone penetrating features 1000 to be inserted into the cortical region of the host bone.

In alternative embodiments (not shown), the bone penetrating features may be placed on other locations on the scaffold that do not block access to the apertures, such as at the lateral aspects, in the center, or along the midline of the scaffold. In other alternative embodiments, a scaffold may have multiple bone penetrating features positioned across bone-facing surface of the scaffold in such a manner that unwanted bone penetrating features can be easily removed, cut, or broken off to customize the position of the bone penetrating features on the scaffold.

Figure 12:
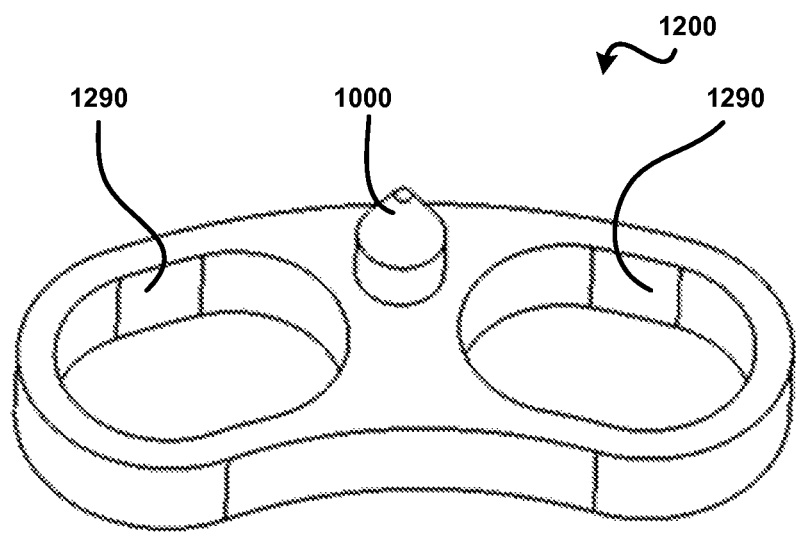
FIG. 12 is a perspective view illustrating a scaffold according to another alternative embodiment of the invention.

Referring to FIG. 12, a perspective view illustrates a scaffold 1200 according to another alternative embodiment of the invention. The scaffold 1200 may be generally half the size of the scaffold 600. The scaffold 1200 may have a shape generally similar to that of the scaffold 600, but may extend along a smaller arc. The scaffold 1200 may have only two apertures 1290 and one bone penetrating feature 1000, as shown. In addition to the half-size embodiment of FIG. 12, scaffolds may be made available in a variety of fractional sizes to accommodate varying anatomy and surgical indications.

In alternative embodiments, scaffolds according to the invention may be offered in a number of modular configurations. A one-piece scaffold may have perforations, ribs, or other features that allow the scaffold to break apart in predetermined fractional sizes and shapes. The fractional sizes may also be manufactured such that two or more units can connect or interlock with each other forming an assembly of scaffolds. Multiple scaffolds may be stacked to form a thicker scaffold. Two connectable half sizes may be provided in a left and right configuration that may be assembled to form a full size assembled scaffold, or fractional sizes may be provided that allow for two or more units to be linked together. The interlocking mechanism may be accomplished using a number of different methods including a tongue in groove, puzzle piece interlock, post in hole, or other snap-in features. The unused portions at the terminal ends of the final construct may be trimmed off, if necessary, to ensure the ends of the implant have smooth edges. Exemplary modular scaffolds will be shown and described in connection with FIGS. 13-25, as follows.

Figure 13:
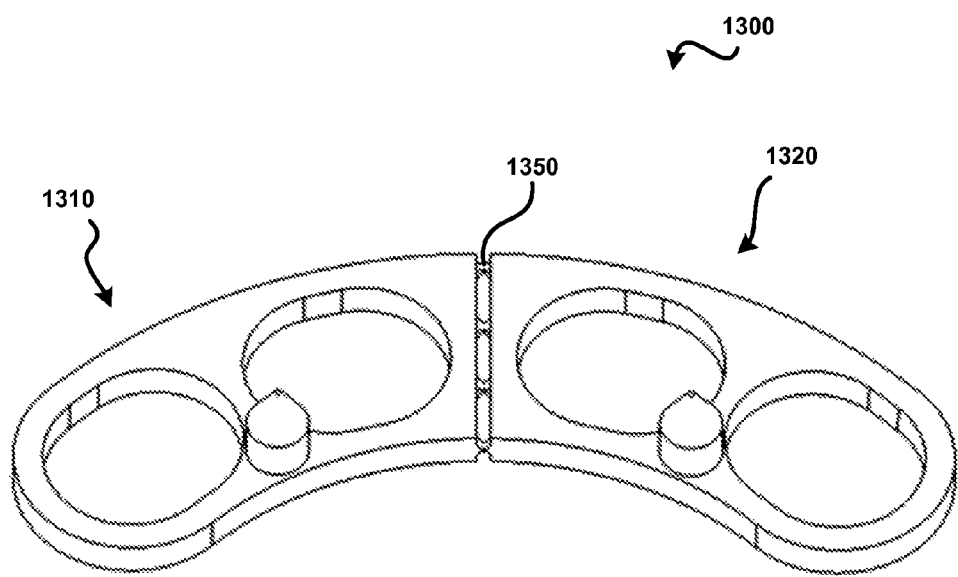
FIG. 13 is a perspective view illustrating a frangible scaffold that is breakable into a first scaffold and a second scaffold, according to another alternative embodiment of the invention.

Referring to FIG. 13, a perspective view illustrates a frangible scaffold 1300 that is breakable into a first scaffold 1310 and a second scaffold 1320, according to another alternative embodiment of the invention. The first scaffold 1310 and the second scaffold 1320 may be formed as a single piece with each other and may be connected together by a breaking feature 1350 that provides a weak point in the construction of the frangible scaffold 1300. Thus, the frangible scaffold 1300 breaks relatively easily at the breaking feature 1350. The frangible scaffold 1300 may be designed to be broken by hand without any additional tooling, or may be designed to break when a suitable tool is used to apply the appropriate bending force to the frangible scaffold 1300 to cause the frangible scaffold to break at the breaking feature 1350.

In the example of FIG. 13, the breaking feature 1350 may be a notch formed in the material of the frangible scaffold. In alternative embodiments, breaking features such as pre-stressed regions, perforated regions, regions formed of a weaker material, and the like may be used in place of a notch.

Figure 14:
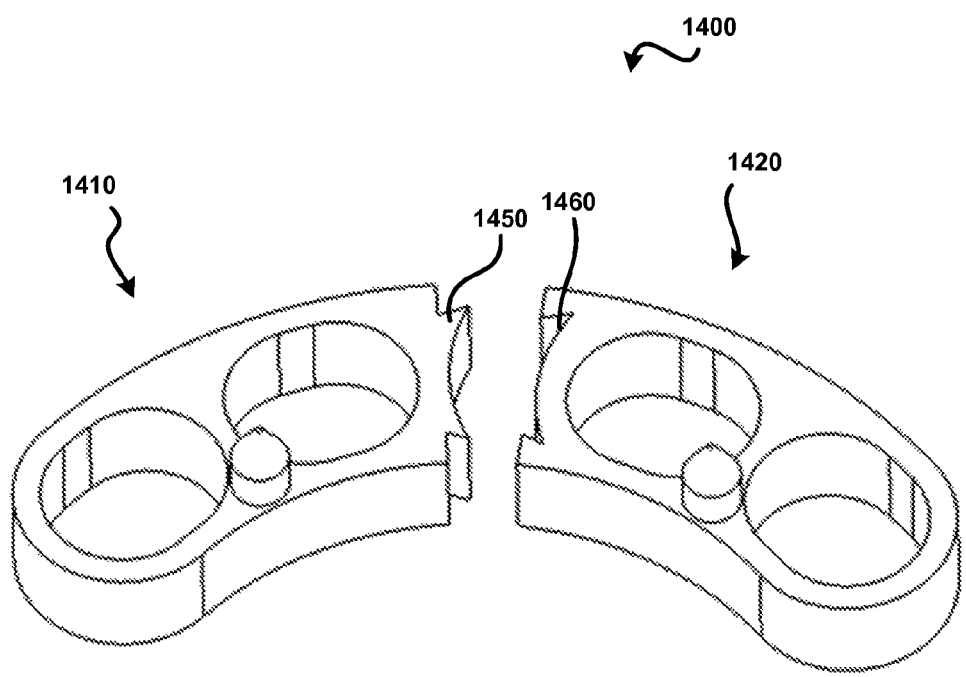
FIG. 14 is a perspective view illustrating first and second scaffolds that are attachable together according to another alternative embodiment of the invention.

Referring to FIG. 14, a perspective view illustrates a modular scaffold 1400 including a first scaffold 1410 and a second scaffold 1420 that are attachable together according to another alternative embodiment of the invention. More specifically, the first scaffold 1410 may have an attachment feature 1450 and the second scaffold 1420 may have an attachment feature 1460 attachable to the attachment feature 1450 of the first scaffold 1410. In the embodiment of FIG. 14, the attachment feature 1450 and the attachment feature 1460 may interlock such that they can only be detached from each other by moving the second scaffold 1420 out of plane relative to the first scaffold 1410. Thus, for an application in which a larger scaffold is desired, the first scaffold 1410 and the second scaffold 1420 may be rapidly and securely attached together, and may be expected to remain attached together during application of the bone cement.

If desired, the attachment feature 1450 and the attachment feature 1460 may have detents or other features that snap together, tactilely or audibly, to hold them together as they are placed on the bone and/or to confirm to the user that they have been fully attached together. In alternative embodiments, attachment features may have a wide variety of configurations including a number of complex shapes. Such attachment features may function similar to puzzle pieces that can be put together along one plane but may not be pulled apart in another plane. Additional features may be present on the scaffolds that lock the scaffolds in multiple planes, preventing unintentional disassembly.

Figure 15:
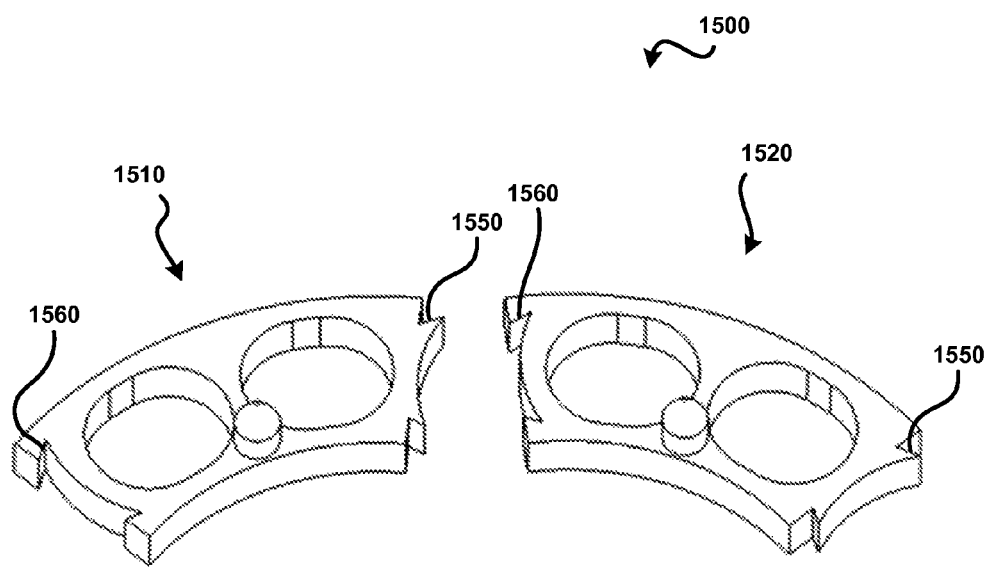
FIG. 15 is a perspective view illustrating first and second scaffolds that are attachable together according to another alternative embodiment of the invention.

Referring to FIG. 15, a perspective view illustrates a modular scaffold 1500 including a first scaffold 1510 and a second scaffold 1520 that are attachable together according to another alternative embodiment of the invention. More precisely, as in the modular scaffold 1400 of FIG. 14, the first scaffold 1510 may have an attachment feature 1550 and the second scaffold 1520 may have an attachment feature 1560 attachable to the attachment feature 1550 of the first scaffold 1510. However, the first scaffold 1510 may also have an attachment feature 1560 on the opposite end of the first scaffold 1510 from the attachment feature 1550, and the second scaffold 1520 may also have an attachment feature 1550 on the opposite side of the second scaffold 1520 from the attachment feature 1560.

Thus, the first scaffold 1510 and the second scaffold 1520 may be substantially identical. Accordingly, any number of the first scaffold 1510 and/or the second scaffold 1520 may be attached together end-to-end to provide a modular scaffold of the desired length and/or curvature. If desired, the attachment feature 1550 and/or the attachment feature 1560 at the unattached ends of the first scaffold 1510 and/or the second scaffold 1520 may be cut away, shaved off, or otherwise removed to eliminate sharp edges prior to implantation. Further, if desired, more than one of the first scaffold 1510 and/or the second scaffold 1520 may also be stacked one on top of another to permit variation in the thickness as well as the length of the modular scaffold. If desired, registration features (not shown) such as posts, holes, detents, and the like may be formed in the adjoining surfaces of the first scaffold 1510 and/or the second scaffold 1520 to facilitate alignment for stacking.

In alternative embodiments, such modular scaffolds may not be identically shaped or sized, but may rather come in a variety of shapes and/or sizes. For example, a kit may contain a variety of scaffolds including scaffolds with various lengths, radii of curvature, thicknesses, and the like. Dissimilar scaffolds may be attached together to provide a modular scaffold with the desired shape.

Figure 16:
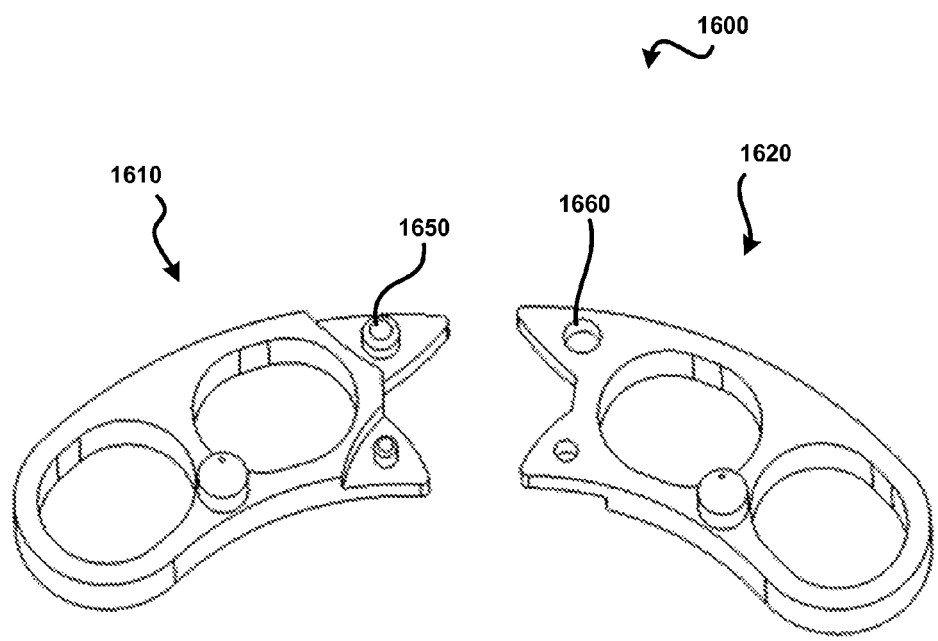
FIG. 16 is a perspective view illustrating first and second scaffolds that are attachable together according to another alternative embodiment of the invention.

Referring to FIG. 16, a perspective view illustrates a modular scaffold 1600 including a first scaffold 1610 and a second scaffold 1620 that are attachable together according to another alternative embodiment of the invention. As shown, the first scaffold 1610 may have an attachment feature 1650 and the second scaffold 1620 may have an attachment feature 1660 attachable to the attachment feature 1650 of the first scaffold 1610. As in the embodiments of FIGS. 14 and 15, the attachment feature 1650 and the attachment feature 1660 may interlock such that they can only be detached from each other by moving the second scaffold 1620 out of plane relative to the first scaffold 1610.

As illustrated, the attachment feature 1650 may include one or more posts or extrusions, while the attachment feature 1660 may contain one or more holes or bores. The posts of the attachment feature 1650 may be inserted into the holes of the attachment feature 1660 to connect the first scaffold 1610 to the second scaffold 1620. The posts of the attachment feature 1660 may be of varying size and geometry. The posts shown in FIG. 16 are cylindrical, but in alternative embodiments (not shown), other shapes may be used, including but not limited to oval shapes, square shapes, triangular shapes, and other polygonal shapes. In such embodiments, the holes may or may not have a similar cross sectional shape similar to that of the posts. For instance, a cylindrical post may interface with a square hole creating a press-fit between the two components at four locations. This may allow the two scaffolds to snap to each other without additional locking features.

Figure 17:
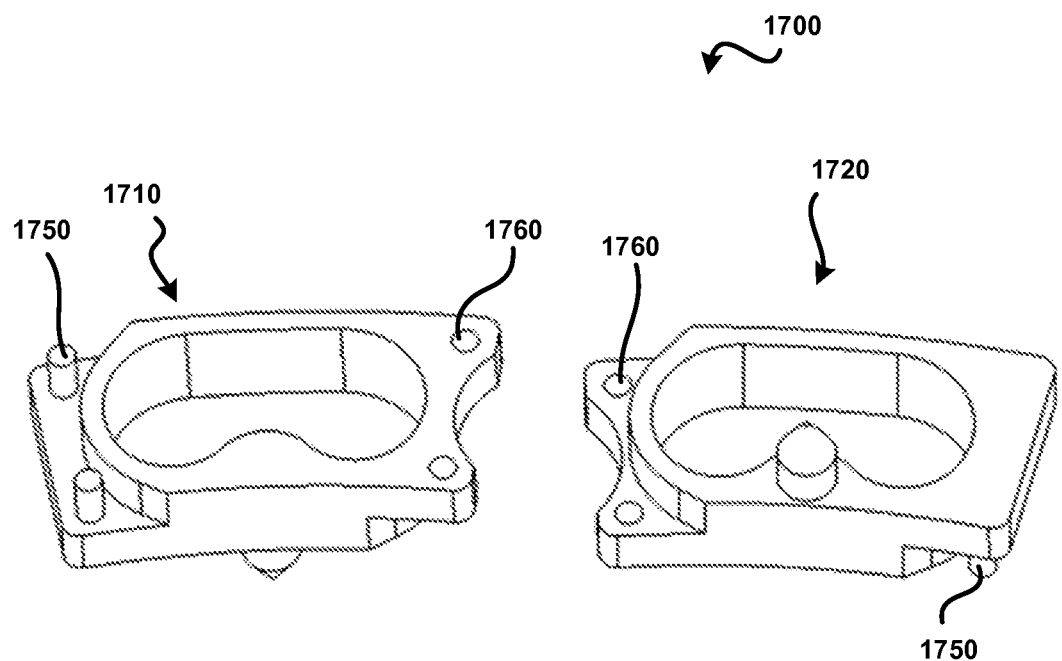
FIG. 17 is a perspective view illustrating first and second scaffolds that are attachable together according to another alternative embodiment of the invention.

Referring to FIG. 17, a perspective view illustrates a modular scaffold 1700 including a first scaffold 1710 and a second scaffold 1720 that are attachable together according to another alternative embodiment of the invention. Like the modular scaffold 1500 of FIG. 15, each of the first scaffold 1710 and the second scaffold 1720 may have an attachment feature 1750 at one end, and an attachment feature 1760 at its opposite end. The second scaffold 1720 may be substantially identical to the first scaffold 1710. The second scaffold 1720 is shown in an opposite orientation relative to the first scaffold 1710 to enable the attachment feature 1750 and the attachment feature 1760 to be viewed from both sides.

As in the modular scaffold 1600 of FIG. 16, each attachment feature 1750 may include posts, which may be inserted in to holes of an attachment feature 1760 to attach the first scaffold 1710 to the second scaffold 1720. As in the modular scaffold 1500 of FIG. 15, more than two scaffolds may be attached together, end-to-end, until a modular scaffold with the desired size and/or shape has been constructed.

Figure 18:
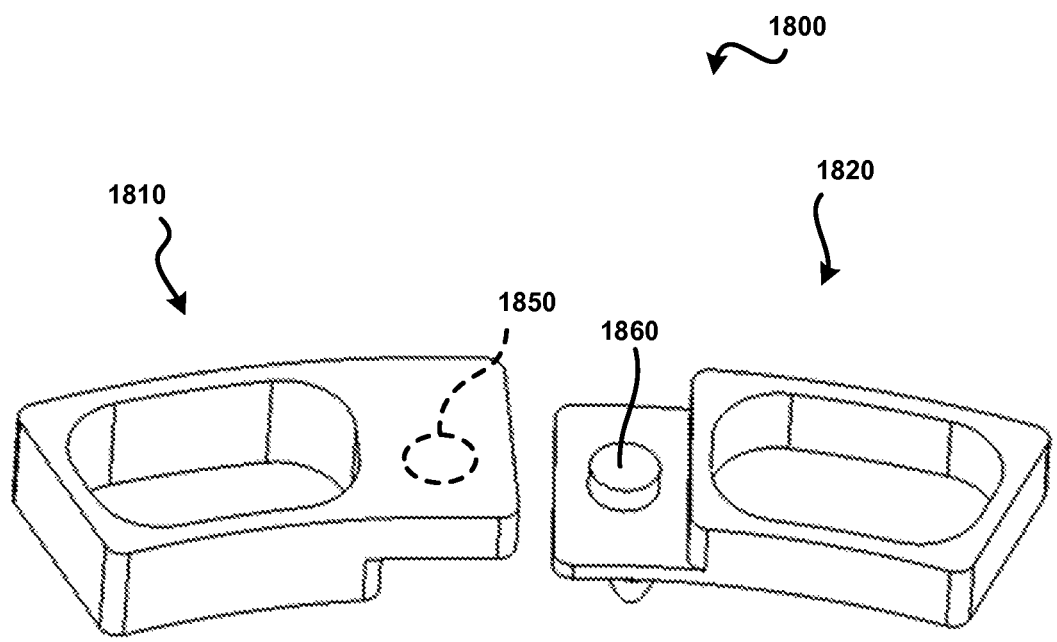
FIG. 18 is a perspective view illustrating first and second scaffolds that are attachable together according to another alternative embodiment of the invention.

Referring to FIG. 18, a perspective view illustrates a modular scaffold 1800 including a first scaffold 1810 and a second scaffold 1820 that are attachable together according to another alternative embodiment of the invention. As in previous embodiments, the first scaffold 1810 may have an attachment feature 1850 attachable to an attachment feature 1860 of the second scaffold 1820. The attachment feature 1850 may include a blind hole, and the attachment feature 1860 may include a shortened post designed to be received in the blind hole of the attachment feature 1850.

Figure 19:
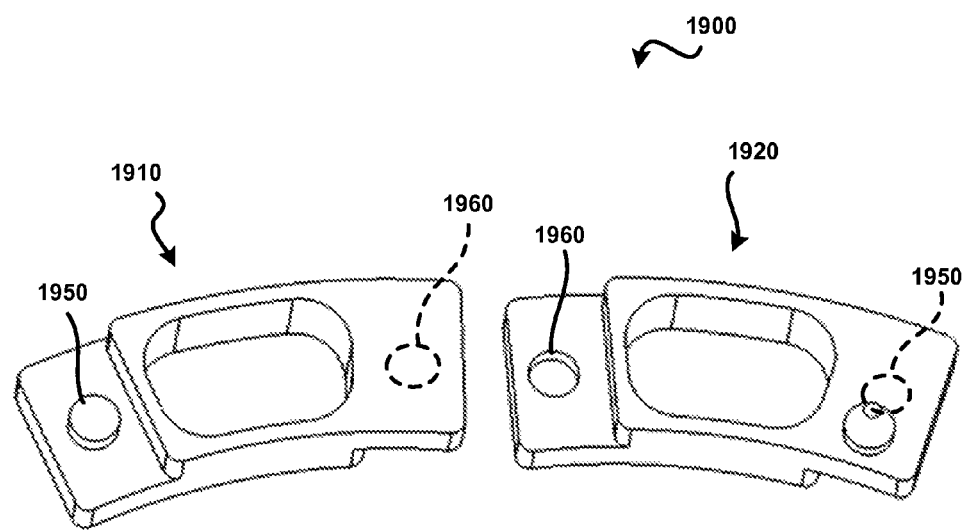
FIG. 19 is a perspective view illustrating first and second scaffolds that are attachable together according to another alternative embodiment of the invention.

Referring to FIG. 19, a perspective view illustrates a modular scaffold 1900 including a first scaffold 1910 and a second scaffold 1920 that are attachable together according to another alternative embodiment of the invention. Like the modular scaffold 1500 of FIG. 15, each of the first scaffold 1910 and the second scaffold 1920 may have an attachment feature 1950 at one end, and an attachment feature 1960 at its opposite end. The second scaffold 1920 may be substantially identical to the first scaffold 1910. The second scaffold 1920 is shown in an opposite orientation relative to the first scaffold 1910 to enable the attachment feature 1950 and the attachment feature 1960 to be viewed from both sides.

As in the modular scaffold 1800 of FIG. 18, each attachment feature 1950 may include a post, which may be inserted in to a blind hole of an attachment feature 1960 to attach the first scaffold 1910 to the second scaffold 1920. As in the modular scaffold 1500 of FIG. 15, more than two scaffolds may be attached together, end-to-end, until a modular scaffold with the desired size and/or shape has been constructed.

Figure 20:
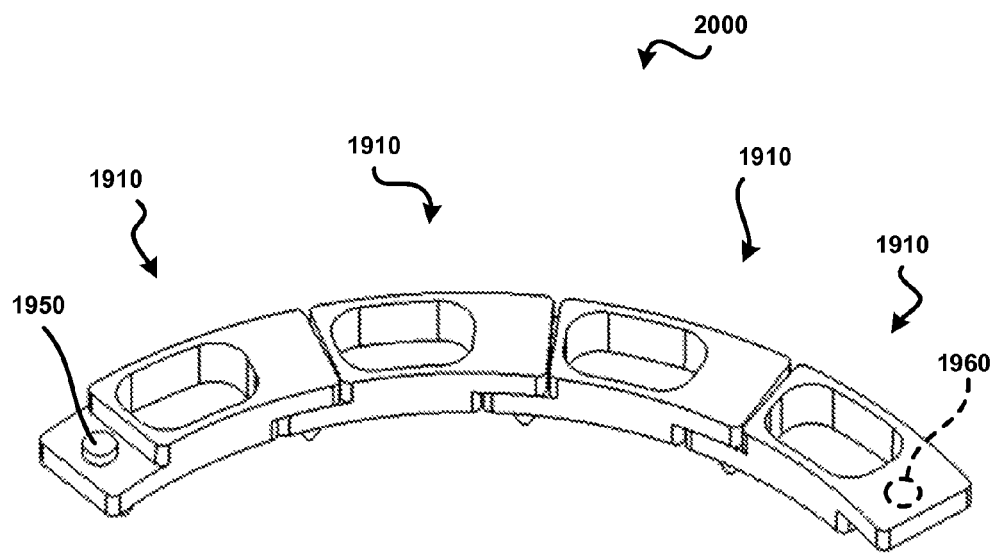
FIG. 20 is a perspective view illustrating first, second, third, and fourth scaffolds that are attachable together according to another alternative embodiment of the invention.

Referring to FIG. 20, a perspective view illustrates a modular scaffold 2000 including four copies of the first scaffold 1910 of FIG. 19, attached together according to another alternative embodiment of the invention. As mentioned previously, any number of scaffolds may be attached together end-to-end to provide a modular scaffold with the desired size and/or shape.

Figure 21:
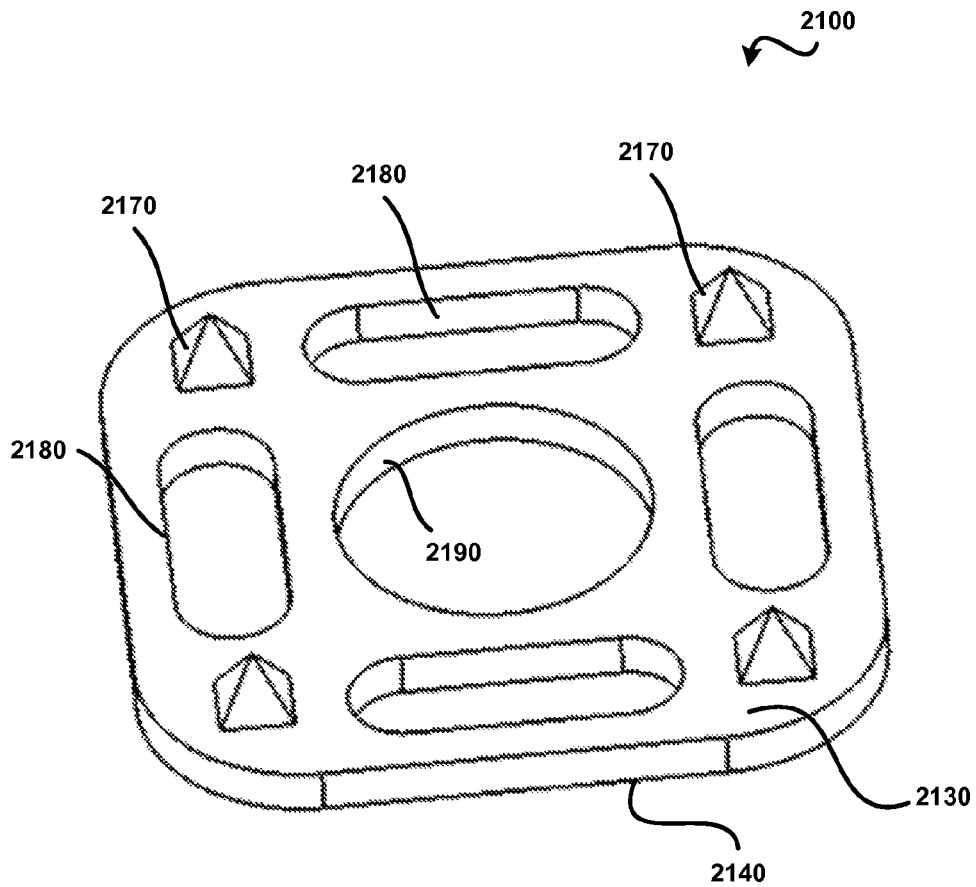
FIG. 21 is a perspective view illustrating a scaffold according to another alternative embodiment of the invention.

Referring to FIG. 21, a perspective view illustrates a scaffold 2100 according to another alternative embodiment of the invention. The scaffold 2100 may have a shape that is substantially rectangular or even square. In alternative embodiments (not shown), scaffolds may be triangular, square, trapezoidal, round, oval, or otherwise polygonal. The scaffold 2100 may have a bone-facing surface 2130 and a joint-facing surface 2140, with a number of slots 2180 that pass through the scaffold 2100 from the bone-facing surface 2130 to the joint-facing surface 2140. In the center of the scaffold 2100, an aperture 2190 may be present to accommodate a stem or post that is present on the arthroplasty prosthesis to be used in conjunction with the scaffold 2100. For example, the scaffold 2100 may be used for a femoral arthroplasty prosthesis like the femoral arthroplasty prosthesis 110 of FIG. 1. The slots 2180 may accommodate the passage of host bone and/or bone cement 700. The scaffold 2100 may also have one or more bone penetrating features 2170 on the bone-facing surface 2130. These bone penetrating features 2170 may aid in the fixation of the scaffold 2100 to the underlying host bone. The bone penetrating features 2170 are shown with generally pyramidal shapes, but may have a number of other shapes including a cylindrical, conical rectangular, cubic, complex, or other shapes.

As will be shown and described subsequently, multiple scaffolds 2100 may be stacked on top of each other. The bone penetrating features 2170 may act as registration features, and may register with corresponding divots or other features on the joint-facing surface 2140.

Figure 22:
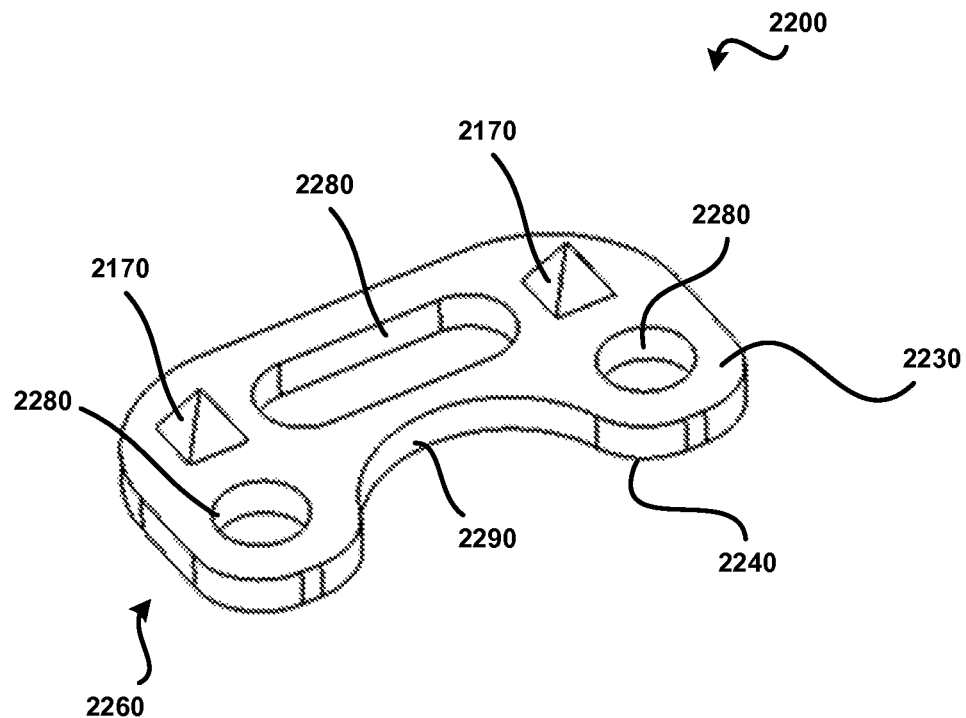
FIG. 22 is a perspective view illustrating a scaffold according to another alternative embodiment of the invention.

Referring to FIG. 22, a perspective view illustrates a scaffold 2200 according to another alternative embodiment of the invention. The scaffold 2200 may be, generally, a half-sized version of the scaffold 2100 of FIG. 21. The scaffold 2200 may have features similar to those of the scaffold, and may thus have a bone-facing surface 2230, a joint-facing surface 2240, and a series of apertures 2280 that pass between the bone-facing surface 2230 and the joint-facing surface 2240. The apertures 2280 may include multiple shapes. The scaffold 2200 may also have a plurality of bone penetrating features 2170.

The scaffold 2200 may also have an exterior scaffold wall 2260. The exterior scaffold wall 2260 may be shaped to define an aperture 2290 that is generally semicircular in shape. The aperture 2290 may accommodate a protruding element of an arthroplasty prosthesis such as a bone anchoring stem of the femoral arthroplasty prosthesis 110 of FIG. 1.

Figure 23:
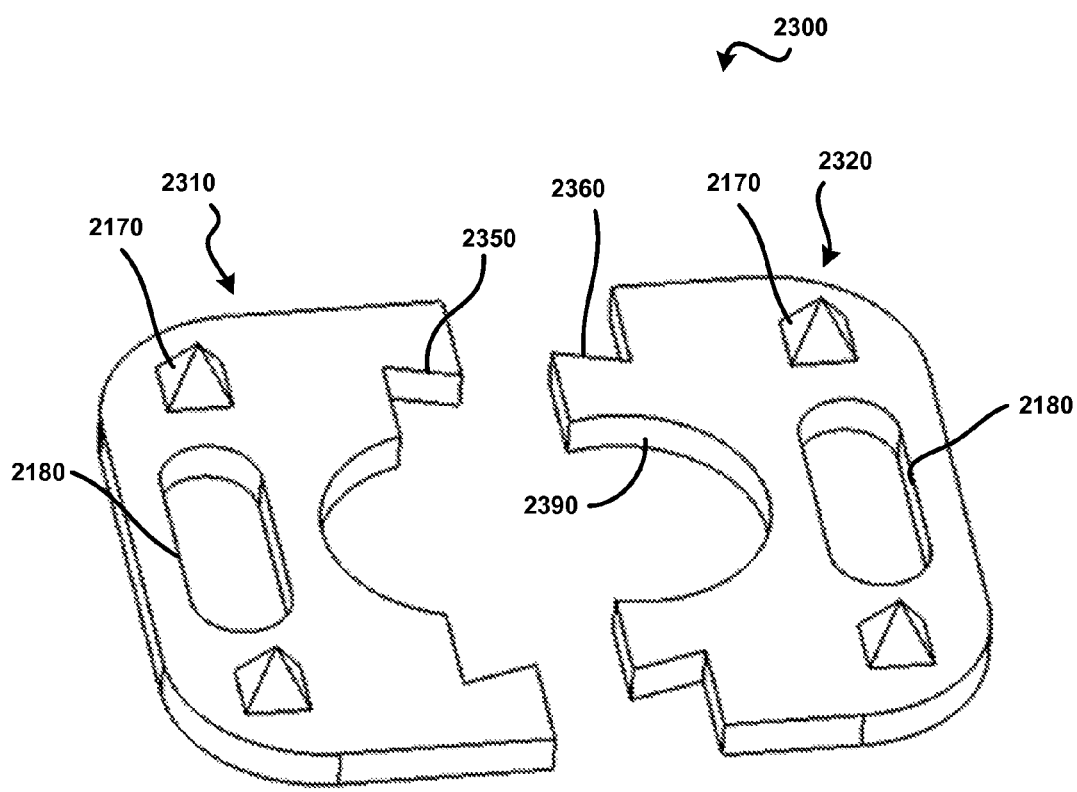
FIG. 23 is a perspective view illustrating first and second scaffolds that are attachable together according to another alternative embodiment of the invention.

Referring to FIG. 23, a perspective view illustrates a modular scaffold 2300 including a first scaffold 2310 and a second scaffold 2320 that are attachable together according to another alternative embodiment of the invention. The first scaffold 2310 may have an attachment feature 2350 that is attachable to an attachment feature 2360 of the second scaffold 2320. As embodied in FIG. 23, the attachment feature 2350 and the attachment feature 2360 may include dovetail features like the attachment feature 1450 and the attachment feature 1460 of FIG. 14. Thus, as in FIG. 14, the attachment feature 2350 and the attachment feature 2360 may require out-of-plane motion of the second scaffold 2320 relative to the first scaffold 2310 to detach the second scaffold 2320 from the first scaffold 2310.

The first scaffold 2310 and the second scaffold 2320 may have bone penetration features 2170 and slots 2180 like those of the scaffold 2100 of FIG. 21. The first scaffold 2310 and the second scaffold 2320, when attached together, may define an aperture 2390 similar in function to the aperture 2190 of FIG. 21. However, the aperture 2390 may advantageously be built around a bone engagement stem or other feature that is already in place relative to the bone.

Figure 24:
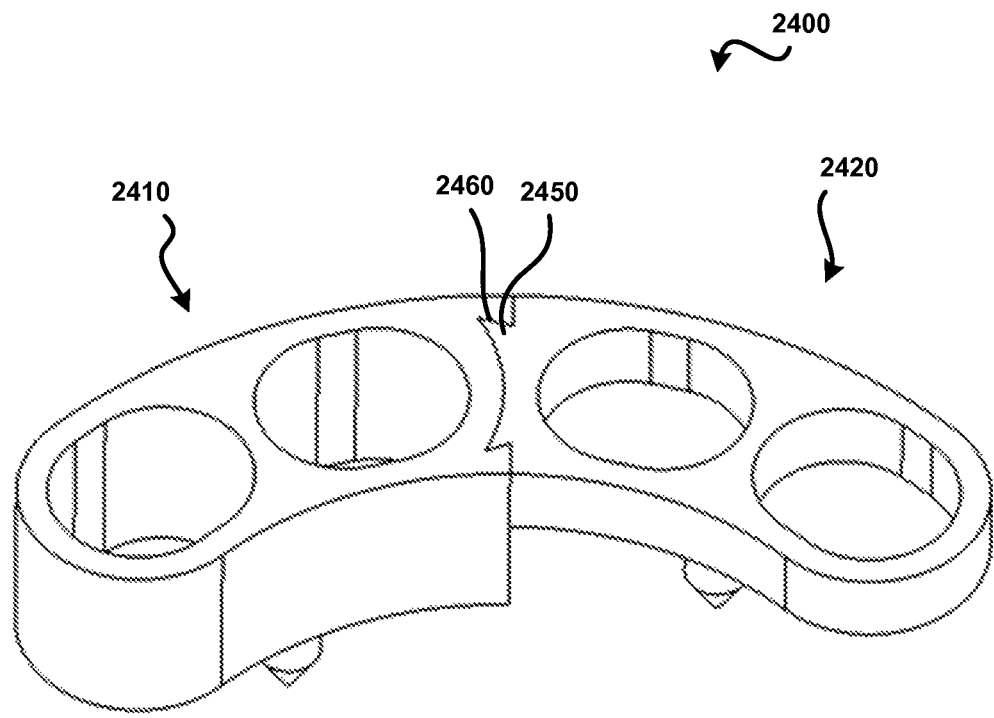
FIG. 24 is a perspective view illustrating first and second scaffolds that are attachable together according to another alternative embodiment of the invention.

Referring to FIG. 24, a perspective view illustrates a modular scaffold 2400 including a first scaffold 2410 and a second scaffold 2420 that are attachable together according to another alternative embodiment of the invention. The first scaffold 2410 may have an attachment feature 2450 that is attachable to an attachment feature 2460 of the second scaffold 2420. As embodied in FIG. 24, the attachment feature 2450 and the attachment feature 2460 may include dovetail features like the attachment feature 1450 and the attachment feature 1460 of FIG. 14.

The modular scaffold 2400 may be different from the other modular scaffolds illustrated previously in that the first scaffold 2410 may have a thickness much larger than a thickness of the second scaffold 2420. Thus, the modular scaffold 2400 may be particularly helpful for situations in which the raised surface to be formed with bone cement is not parallel to the target surface on which the modular scaffold 2400 is placed. If desired, the greater thickness of the first scaffold 2410 may be used to compensate for divots or other bone deformities present under the position of the first scaffold 2410. The difference in thickness between the first scaffold 2410 and the second scaffold 2420 is large in the embodiment shown, but may be smaller or greater in other embodiments.

Figure 25:
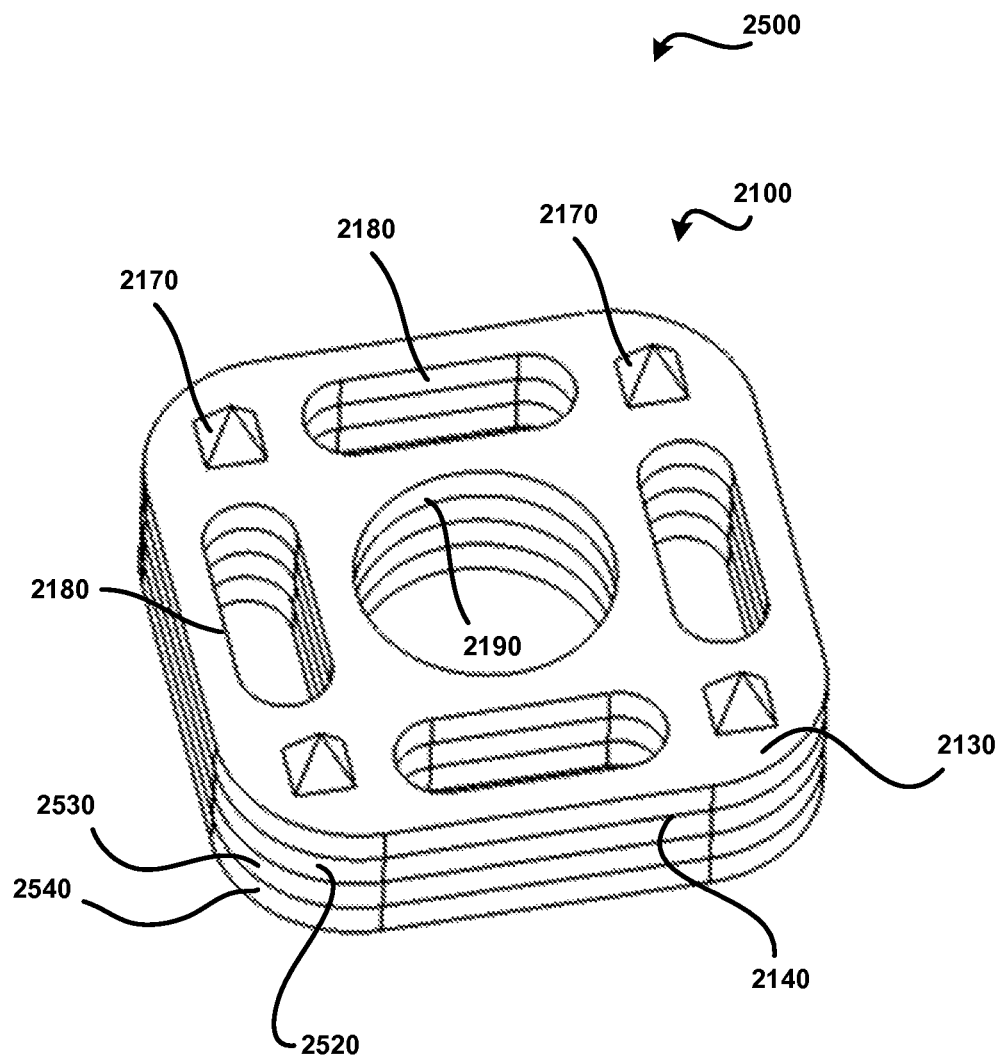
FIG. 25 is a perspective view illustrating the scaffold of FIG. 21 stacked with three other scaffolds according to another alternative embodiment of the invention.

Referring to FIG. 25, a perspective view illustrates a modular scaffold 2500 including the scaffold 2100 of FIG. 21 stacked with a second scaffold 2520, a third scaffold 2530, and a fourth scaffold 2540 according to another alternative embodiment of the invention. Any number of scaffolds may be stacked to provide a modular scaffold with the necessary height. As mentioned previously, the scaffold 2100 may have, on its joint-facing surface 2140, divots, detents, or other features that register with bone penetrating features of the scaffold to be placed on top of it. Such divots, detents, or other features, along with the bone penetrating features 2170, may thus act as registration features by helping align the scaffold 2100 with the second scaffold 2520, the third scaffold 2530, and/or the fourth scaffold 2540.

The second scaffold 2520, the third scaffold 2530, and/or the fourth scaffold 2540 may be substantially identical to the scaffold 2100. Alternatively, the second scaffold 2520, the third scaffold 2530, and/or the fourth scaffold 2540 may be different from the scaffold 2100 in that they have different dimensions, such as different heights. Having some stacked scaffolds thinner than others may enhance the surgeon's ability to fine-tune the height of the stack.

Figure 26:
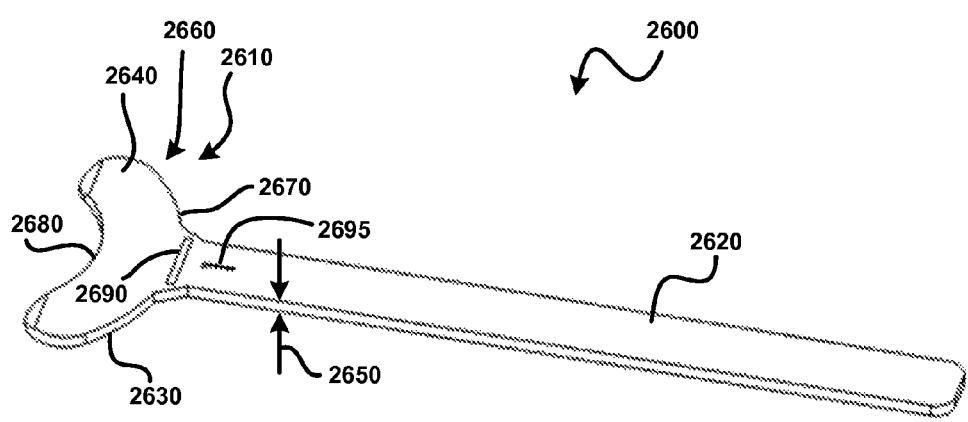
FIG. 26 is a perspective view illustrating a trial scaffold according to one embodiment of the invention.

Referring to FIG. 26, a perspective view illustrates a trial scaffold 2600 according to one embodiment of the invention. Like the trial scaffold 400 of FIG. 4, the trial scaffold 2600 may have a main body 2610 and a handle 2620 extending from the main body 2610. The main body 2610 may have a shape that approximates that of a scaffold, such as the scaffold 600. Thus, the main body 2610 may have a bone-facing trial surface 2630 and a joint-facing trial surface 2640, which may optionally be parallel to each other as shown to provide a thickness 2650 that is substantially uniform across the bone-facing trial surface 2630 and across the joint-facing trial surface 2640. If desired, the joint-facing trial surface 2640 may instead be angled relative to the bone-facing trial surface 2630, as indicated in the description of the trial scaffold 400.

The bone-facing trial surface 2630 and the joint-facing trial surface 2640 may cooperate to define an exterior trial scaffold wall 2660. The exterior trial scaffold wall 2660 may have a curved shape with a convex portion 2670 and a concave portion 2680. The concave portion 2680 may be positioned on the opposite side of the exterior trial scaffold wall 2660 from the convex portion 2670, providing the main body 2610 with a kidney shape. As in the trial scaffold 400 described previously, the convex portion 2670 may have shape matched to that of the convex portion 490 of the resection surface 310. The concave portion 2680 may be oriented toward the hole 340.

The trial scaffold 2600 may have a ridge 2690 that facilitates proper placement of the main body 2610 relative to the host bone. More specifically, a surgeon may insert the main body 2610 onto the target portion 330 of the resection surface 310 by sliding the main body 2610 on the target portion 330 until the ridge 2690 reaches the outer edge of the resection surface 310. The ridge 2690 may be positioned such that, when the ridge 2690 abuts the outer edge of the resection surface 310, the main body 2610 is at an optimal position to rest on cortical bone. This may increase the likelihood that the scaffold 600 will also be placed to rest on cortical bone.

The trial scaffold 2600 may be different from the trial scaffold 400 in that the thickness 2650 of the trial scaffold 2600 may be much less than that of the trial scaffold 400. This may facilitate usage of the trial scaffold 2600 with thinner scaffolds, such as the frangible scaffold 1300 of FIG. 13. Alternatively, the thickness 2650 may enable the trial scaffold 2600 to be stacked with other trial scaffolds in a manner that facilitates adjustment of the overall height of the set of trial scaffolds placed on the target portion 330 of the resection surface 310. The handle 2620 may include a marking 2695 for this purpose. One exemplary trial scaffold kit will be shown and described in connection with FIG. 27.

Figure 27:
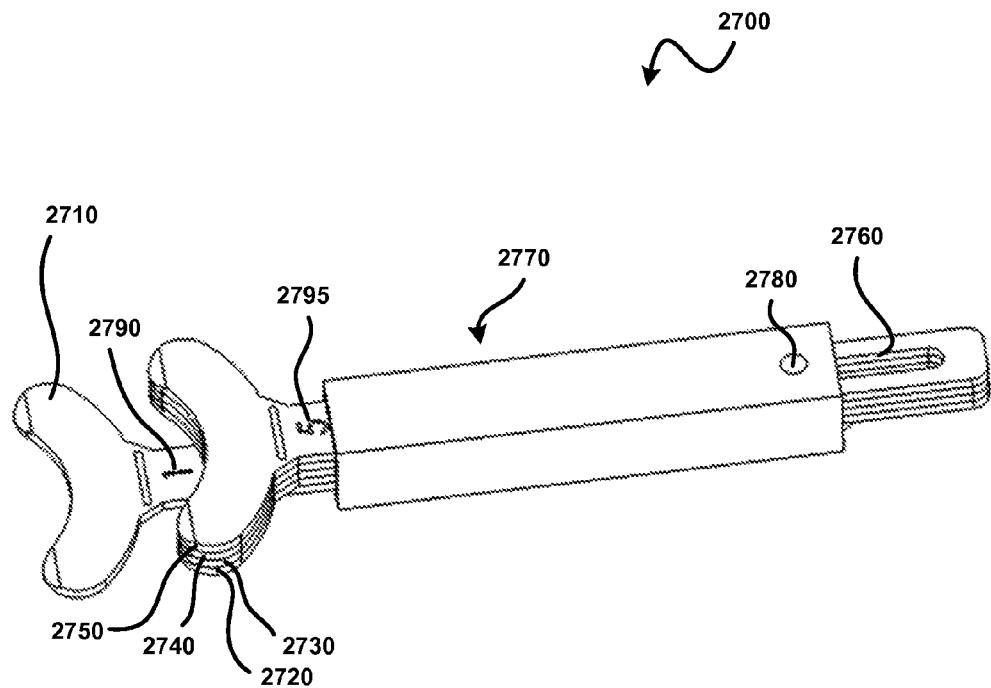
FIG. 27 is a perspective view illustrating a kit of trial scaffolds according to one embodiment of the invention.

Referring to FIG. 27, a perspective view illustrates a trial scaffold kit 2700 including a first trial scaffold 2710 similar to the trial scaffold 2600 of FIG. 26 along with a second trial scaffold 2720, a third trial scaffold 2730, a fourth trial scaffold 2740, and a fifth trial scaffold 2750. If desired, the second trial scaffold 2720, the third trial scaffold 2730, the fourth trial scaffold 2740, and the fifth trial scaffold 2750 may all be substantially identical to the first trial scaffold 2710, except that each of them may have a different marking. For example, a marking 2790 on the first trial scaffold 2710 may indicate that the first trial scaffold 2710 is number one. The second trial scaffold 2720, the third trial scaffold 2730, the fourth trial scaffold 2740, and the fifth trial scaffold 2750 may be marked no.'s two through five, respectively. A marking 2795 is visible on the fifth trial scaffold 2750. Each of the trial scaffolds may also have a slot 2760 running longitudinally along its handle.

The trial scaffold kit 2700 may also have a holder 2770 that retains the stems of the first trial scaffold 2710, the second trial scaffold 2720, the third trial scaffold 2730, the fourth trial scaffold 2740, and the fifth trial scaffold 2750. The holder 2770 may have a boxlike shape with a hollow interior. A pin 2780 may pass through the holder 2770, and may also pass through the slot 2760 of each of the first trial scaffold 2710, the second trial scaffold 2720, the third trial scaffold 2730, the fourth trial scaffold 2740, and the fifth trial scaffold 2750 to capture the stems of the trial scaffolds within the holder 2770 and control their range of translating motion relative to the holder 2770.

The trial scaffold kit 2700 may facilitate fit and function testing by enabling the surgeon to build a trial scaffold of the desired thickness on the target portion 330 of the resection surface 310. More precisely, the surgeon may withdraw any number of the trial scaffolds from the holder 2770 and line them up directly on top of each other. The markings may provide easy visualization of the thickness of the resulting trial scaffold (i.e., from one millimeter, if only the first trial scaffold 2710 is withdrawn from the holder 2770, all the way up to five millimeters, if all of the trial scaffolds are withdrawn from the holder 2770). In FIG. 27, the trial scaffolds all have the same thickness. In alternative embodiments, trial scaffolds with different thicknesses may be combined together to facilitate fine-tuning of the overall thickness.

Figure 28:
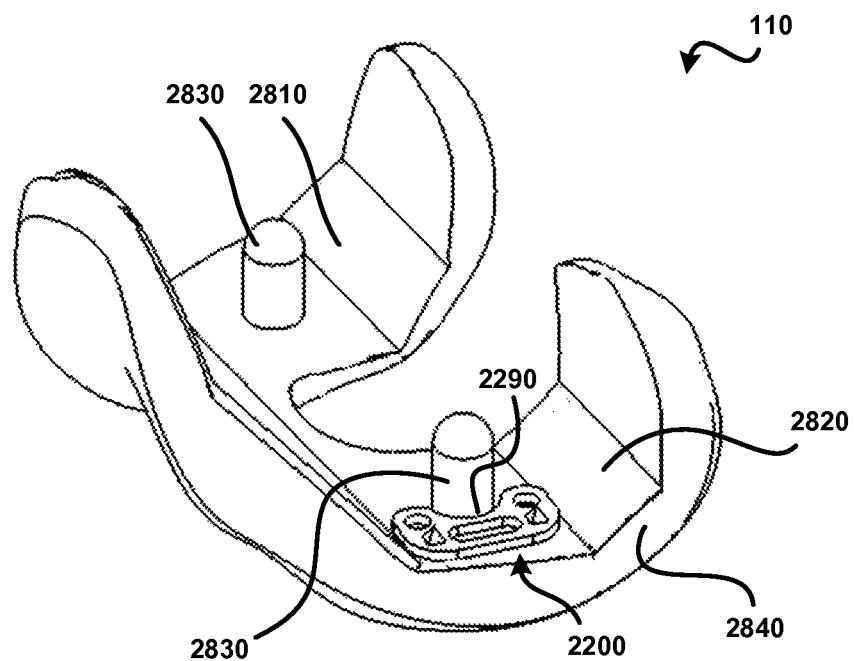
FIG. 28 is a perspective view illustrating a femoral arthroplasty prosthesis with a scaffold according to another embodiment of the invention.

Referring to FIG. 28, a perspective view illustrates the femoral arthroplasty prosthesis 110 of FIG. 1 with the scaffold 2200 of FIG. 22 positioned to be placed on a target surface (not shown) on a resection surface on the distal end of the femur 100. As shown, the femoral arthroplasty prosthesis 110 may have a first femoral condyle 2810 and a second femoral condyle 2820, each of which provides an articulating surface of the femoral arthroplasty prosthesis 110. Additionally, the femoral arthroplasty prosthesis 110 may have a pair of stems 2830 that extend into corresponding holes (not shown) in the distal end of the femur 100. The first femoral condyle 2810 and the second femoral condyle 2820 may cooperate to define an exterior prosthesis wall 2840 that extends around the periphery of the first femoral condyle 2810 and the second femoral condyle 2820.

The scaffold 2200 may reside, for example, interior to the second femoral condyle 2820, and may be positioned such that the exterior surface of the scaffold 2200 is generally aligned with the exterior prosthesis wall 2840 of the femoral arthroplasty prosthesis 110, and the aperture 2290 of the scaffold 2200 receives the adjacent portion of the stem 2830 extending from the second femoral condyle 2820. Thus, the aperture 2290 may enable the stem 2830 to extend into the corresponding hole on the target surface without interference.

The procedure for using the scaffold 2200 to facilitate provision of a raised surface for placement of the femoral arthroplasty prosthesis 110 may be similar to that set forth in FIG. 2. Additionally, other joints may be replaced and/or revised with very similar procedures.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. §112 Para. 6. It will be apparent to those having skill in the art that changes may be made to the details of the above-described embodiments without departing from the underlying principles of the invention.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

What is claimed is:

1. A method for replacing a knee joint defined by a juncture of a distal end of a femur with a proximal end of tibia, the method comprising:
    removing a first articulating surface from the proximal end of the tibia to expose a resection surface;
    identifying a target portion of the resection surface that is to be preferentially elevated relative to a remainder of the resection surface, wherein the target portion is offset from a geometric center of the resection surface;
    placing a first scaffold on a subset of the target portion of the resection surface, wherein any included scaffold(s) only occupies less than half of the target portion and none of the remainder of the resection surface;

with a majority of the target portion uncovered by any scaffold, positioning cement on the resection surface with a lesser thickness outside the target portion and a greater thickness, retained by the first scaffold, with the cement defining a raised surface with a planar shape covering the entire resection surface; and securing a first joint prosthesis comprising a replacement articulating surface on the raised surface;

wherein the first scaffold comprises a first bone-facing surface and a first joint-facing surface displaced from the first bone-facing surface by a first thickness, the first bone-facing surface comprising a first anchoring feature, integrally formed with the first bone-facing surface, that protrudes from the first bone-facing surface, the first anchoring feature comprising a first tip;

wherein placing the first scaffold on the target portion of the resection surface comprises penetrating the resection surface with the first tip;

wherein positioning the cement on the resection surface comprises keeping the first scaffold in place on the target portion via engagement of the first anchoring feature with the subset of the target portion.

2. The method of claim 1, wherein removing the first articulating surface comprises resecting the proximal end of the tibia at the resection surface to remove a corresponding natural articulating surface.

3. The method of claim 1, wherein removing the first articulating surface comprises removing a primary prosthetic component, wherein the first joint prosthesis comprises a revision prosthetic component.

4. The method of claim 1, wherein a plurality of apertures extend through the first scaffold from the bone-facing surface to the joint-facing surface, wherein placing the first scaffold on the subset of the target portion comprises placing the bone-facing surface on the subset of the target portion, wherein positioning the cement on the subset of the target portion comprises inserting the cement into the apertures, wherein the apertures are further sized such that the apertures, together, have an area twice as large as that of the bone-facing surface that exists outside the apertures.

5. The method of claim 4, wherein positioning the cement on the resection surface comprises forming the raised surface such that the raised surface is substantially flush with the joint-facing surface of the first scaffold.

6. The method of claim 1, further comprising:
removing a second articulating surface from the distal end of the femur; and
securing a second joint prosthesis comprising a second replacement articulating surface to the distal end of the femur.

7. The method of claim 1, further comprising, prior to placing the first scaffold on the subset of the target portion of the resection surface:
selecting a first trial scaffold from a trial scaffold kit comprising the first trial scaffold and a second trial scaffold;
placing the first trial scaffold on the target portion of the resection surface;
placing a trial joint prosthesis on the resected surface and the trial scaffold; and
assessing a position of the trial joint prosthesis.

8. The method of claim 7, further comprising, based on results of assessing the position of the trial joint prosthesis, selecting the first scaffold from a scaffold kit comprising the first scaffold and a second scaffold.

9. The method of claim 1, wherein the first scaffold is formed as a single piece with a second scaffold to define a frangible scaffold comprising a breaking feature between the first scaffold and the second scaffold, the method further comprising, prior to placing the first scaffold on the subset of the target portion of the resection surface, breaking the frangible scaffold to separate the first scaffold from the second scaffold.

10. The method of claim 1, wherein the first scaffold comprises a first attachment feature, the method further comprising, prior to placing the first scaffold on the subset of the target portion of the resection surface, attaching the first attachment feature to a second attachment feature of a second scaffold to define a modular scaffold such that placing the first scaffold on the subset of the target portion of the resection surface comprises placing the modular scaffold on the subset of the target portion of the resection surface such that the first scaffold and the second scaffold both rest on the subset of the target portion.

11. The method of claim 1, wherein the first scaffold comprises a first registration feature, the method further comprising, prior to placing the first scaffold on the subset of the target portion of the resection surface, stacking a second scaffold on top of the first scaffold such that a second registration feature of the second scaffold registers with the first registration feature to align the second scaffold with the first scaffold such that placing the first scaffold on the subset of the target portion of the resection surface comprises placing the first scaffold and the second scaffold, in a stacked configuration, on the subset of the target portion.

12. The method of claim 1, further comprising, prior to placement of the first scaffold on the subset of the target portion:
placing a trial joint prosthesis on the resected surface;
detecting a condition of the trial joint prosthesis, wherein the condition is selected from the group consisting of a varus condition, a valgus condition, an improper flexion gap, and an improper extension gap; and
removing the trial joint prosthesis;
wherein placing the first scaffold on the subset of the target portion comprises positioning the first scaffold proximate a periphery of the resection surface to correct the condition.

13. The method of claim 12, wherein positioning the scaffold proximate the periphery of the resection surface comprises positioning the scaffold such that the scaffold rests on cortical bone.

14. A method for replacing a knee joint defined by a juncture of a distal end of a femur with a proximal end of tibia, the method comprising:
removing a first articulating surface from the proximal end of the tibia to expose a resection surface, the resection surface comprising a hole;
identifying a target portion of the resection surface that is to be preferentially elevated relative to a remainder of the resection surface;
placing a first scaffold on a subset of the target portion of the resection surface, offset from the hole, wherein any included scaffold(s) only occupies less than half of the target portion and none of the remainder of the resection surface;
with a majority of the target portion uncovered by any scaffold, positioning cement on the resection surface with a lesser thickness outside the target portion and a greater thickness, retained by the first scaffold, with the cement defining a raised surface with a planar shape covering the entire resection surface except for the hole;
placing a first joint prosthesis comprising a stem and a replacement articulating surface on the raised surface such that the stem extends into the hole; and
securing the first joint prosthesis on the raised surface;
wherein the first scaffold comprises a first bone-facing surface and a first joint-facing surface displaced from the first bone-facing surface by a first thickness, the first bone-facing surface comprising a first anchoring feature, integrally formed with the first bone-facing surface, that protrudes from the first bone-facing surface, the first anchoring feature comprising a first tip;

wherein placing the first scaffold on the target portion of the resection surface comprises penetrating the resection surface with the first tip;

wherein positioning the cement on the resection surface comprises keeping the first scaffold in place on the target portion via engagement of the first anchoring feature with the subset of the target portion.

15. The method of claim 14, further comprising, prior to placement of the first scaffold on the subset of the target portion:

placing a trial joint prosthesis on the resected surface;

detecting a condition of the trial joint prosthesis, wherein the condition is selected from the group consisting of a varus condition, a valgus condition, an improper flexion gap, and an improper extension gap; and removing the trial joint prosthesis;

wherein placing the first scaffold on the target portion comprises positioning the first scaffold proximate a periphery of the resection surface to correct the condition;

wherein positioning the scaffold proximate the periphery of the resection surface comprises positioning the scaffold such that the scaffold rests on cortical bone.

* * * * *